US006174886B1

(12) United States Patent
Pineiro et al.

(10) Patent No.: US 6,174,886 B1
(45) Date of Patent: Jan. 16, 2001

(54) ANTIPSYCHOTIC USE OF TRIAZOLO-PYRIDAZINE DERIVATIVES

(75) Inventors: Jose Luis Castro Pineiro, Bishops Stortford; Ruth McKernan, Saffron Walden; Paul John Whiting, Stansted, all of (GB)

(73) Assignee: Merck Sharp & Dohme Ltd., Hoddesdon (GB)

( * ) Notice: Under 35 U.S.C. 154(b), the term of this patent shall be extended for 0 days.

(21) Appl. No.: 09/191,304

(22) Filed: Nov. 12, 1998

(30) Foreign Application Priority Data

Nov. 13, 1997 (GB) .................................................. 9723999

(51) Int. Cl.[7] ...................... C07D 237/12; C07D 471/02; C07D 237/14
(52) U.S. Cl. ..................... 514/248; 514/340; 544/236; 544/239
(58) Field of Search .................... 514/248, 340; 544/236, 239

(56) References Cited

U.S. PATENT DOCUMENTS

| 4,230,705 | 10/1980 | Allen, JR. et al. | 424/250 |
| 4,260,755 | 4/1981 | Moran et al. | 544/236 |
| 4,260,756 | 4/1981 | Moran et al. | 544/236 |
| 4,654,343 | 3/1987 | Albright et al. | 514/248 |

FOREIGN PATENT DOCUMENTS

| 0085840 | 1/1986 | (EP) . |
| 0134946 | 12/1987 | (EP) . |
| WO 98/04559 | 5/1998 | (WO) . |

OTHER PUBLICATIONS

A. Delini–Stula and D. Berdah–Tordjman, "Antipsychotic Effects of Bretazenil, a Partial Benzodiazepine Agonist in Acute Schizophrenia—A Study Group Report," *J. Psychiatric Res.,* vol. 30, (1996), pp. 239–250.

*Primary Examiner*—James O. Wilson
*Assistant Examiner*—Howard Owens
(74) *Attorney, Agent, or Firm*—Shu M. Lee; David L. Rose

(57) ABSTRACT

A class of substituted or 7,8-ring fused 1,2,4-triazolo[4,3-b]pyridazine derivatives, possessing an optionally substituted cycloalkyl, phenyl or heteroaryl substituent at the 3-position and a substituted alkoxy moiety at the 6-position, are selective ligands for $GABA_A$ receptors, in particular having high affinity for the $\alpha 2$ and/or $\alpha 3$ subunit thereof, and are accordingly of benefit in the treatment and/or prevention of psychotic disorders including schizophrenia.

9 Claims, No Drawings

ANTIPSYCHOTIC USE OF TRIAZOLO-PYRIDAZINE DERIVATIVES

The present invention relates to the use of a class of substituted triazolo-pyridazine derivatives in therapy. More particularly, this invention is concerned with the use of substituted 1,2,4-triazolo[4,3-b]pyridazine derivatives which are ligands for $GABA_A$ receptors in the treatment and/or prevention of psychotic disorders including schizophrenia.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, three $\beta$ subunits, three $\gamma$ subunits and one $\delta$ subunit.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, a $\delta$ subunit also exists, but is present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta2/3\gamma2$, $\alpha3\beta\gamma2/3$, $\alpha2\beta\gamma1$, $\alpha5\beta3\gamma2/3$, $\alpha6\beta\gamma2$, $\alpha6\beta\delta$ and $\alpha4\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta2\gamma2$, $\alpha2\beta\gamma2$ or $\alpha3\beta\gamma2$ subunits will possess desirable antipsychotic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of psychotic disorders including schizophrenia with a reduced propensity to cause sedation.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom. Moreover, these publications nowhere disclose or suggest that the compounds described therein might be an effective therapy for psychotic disorders including schizophrenia.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolo-phthalazine ring system with any other functionality. Moreover, these publications nowhere disclose or suggest that the compounds described therein might be an effective therapy for psychotic disorders including schizophrenia.

The present invention provides a new use for a class of triazolo-pyridazine derivatives which possess desirable binding properties at various $GABA_A$ receptor subtypes. The compounds of use in the present invention have good affinity as ligands for the $\alpha2$ and/or $\alpha3$ subunit of the human $GABA_A$ receptor. The compounds of use in this invention may interact more favourably with the $\alpha2$ and/or $\alpha3$ subunit than with the $\alpha1$ subunit. Desirably, the compounds of use in the invention will exhibit functional selectivity in terms of a selective efficacy for the $\alpha2$ and/or $\alpha3$ subunit relative to the $\alpha1$ subunit.

The compounds of use in the present invention are $GABA_A$ receptor subtype ligands having a binding affinity ($K_i$) for the $\alpha2$ and/or $\alpha3$ subunit, as measured in the assay described hereinbelow, of 100 nM or less, typically of 50 nM or less, and ideally of 10 nM or less. The compounds of use in this invention may possess at least a 2-fold, suitably at least a 5-fold, and advantageously at least a 10-fold, selective affinity for the α2 and/or α3 subunit relative to the α1 subunit. However, the use of compounds which are unselective in terms of their binding affinity for the α2 and/or α3 subunit relative to the α1 subunit is also encompassed within the scope of the present invention; such compounds will desirably exhibit functional selectivity in terms of a selective efficacy for the α2 and/or α3 subunit relative to the α1 subunit.

In *J. Psychiatr. Res.*, 1996, 30, 239–250 are presented the results of a clinical efficacy study of bretazenil, a partial benzodiazepine-receptor agonist, in schizophrenic patients with an acute psychotic episode. The results of the study are stated to suggest moderate antipsychotic efficacy of bretazenil in schizophrenic patients. The most frequent adverse reaction reported in the study was sedation, and this may be attributable to the fact that bretazenil is not a functionally selective $GABA_A$ receptor agonist in the sense that it displays comparable efficacy for the α1 subunit as it does for the α2 and/or α3 subunit.

The present invention provides a method for the treatment and/or prevention of psychotic disorders, including schizophrenia, which comprises administering to a patient in need of such treatment an effective amount of a compound of formula I, or a pharmaceutically acceptable salt thereof or a prodrug thereof:

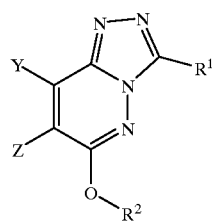

(I)

wherein

Y represents hydrogen or $C_{1-6}$ alkyl; and

Z represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted; or Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl, any of which rings may be optionally benzo-fused and/or substituted;

$R^1$ represents $C_{3-7}$ cycloalkyl, phenyl, furyl, thienyl or pyridinyl, any of which groups may be optionally substituted; and $R^2$ represents cyano($C_{1-6}$)alkyl, hydroxy($C_{1-6}$)alkyl, $C_{3-7}$ cycloalkyl($C_{1-6}$)alkyl, propargyl, $C_{3-7}$ heterocycloalkylcarbonyl($C_{1-6}$)alkyl, aryl($C_{1-6}$)alkyl or heteroaryl($C_{1-6}$)alkyl, any of which groups may be optionally substituted.

The present invention also provides the use of a compound of formula I as defined above, or a pharmaceutically acceptable salt thereof or a prodrug thereof, for the manufacture of a medicament for the treatment and/or prevention of psychotic disorders, including schizophrenia.

Where Y and Z are taken together with the two intervening carbon atoms to form a ring, the resulting compounds of formula I above incorporate the relevant cycloalkenyl, bicycloalkenyl, tetrahydropyridinyl, pyridinyl or phenyl ring fused to the central triazolo-pyridazine ring system as depicted in formula I.

Where Y and Z are taken together with the two intervening carbon atoms to form a $C_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a $C_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6-enyl or bicyclo[3.3.2]dec-9-enyl ring, suitably bicyclo[2.2.1]hept-2-enyl, bicyclo[2.2.2]oct-2-enyl or bicyclo[3.2.2]non-6-enyl, and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, $R^1$ and $R^2$ may be unsubstituted, or substituted by one or more, suitably by one or two, substituents. In general, the groups Y, Z, $R^1$ and $R^2$ will be unsubstituted or monosubstituted. Examples of optional substituents on the groups Y, Z, $R^1$ and $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Illustrative substituents include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, di($C_{1-6}$)alkylaminocarbonyl($C_{1-6}$)alkyl, morpholinyl($C_{1-6}$)alkyl and imidazolyl()alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$)alkoxy.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cycobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof in any proportion is encompassed within the scope of the present invention.

Suitably, Y represents hydrogen or methyl, especially hydrogen.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino. Illustrative values of Z include methyl, ethyl, isopropyl, tert-butyl, methyl-cyclopropyl, cyclobutyl, methyl-cyclobutyl, cyclopentyl, methyl-cyclopentyl, cyclohexyl, phenyl, pyrrolidinyl, methyl-pyrrolidinyl, piperidinyl, morpholinyl, thiomorpholinyl, pyridinyl, furyl, thienyl and chloro-thienyl. Typical values include methyl, ethyl, phenyl, piperidinyl, pyridinyl and thienyl.

In a particular embodiment, the substituent Z represents $C_{3-7}$ cycloalkyl, either unsubstituted or substituted by $C_{1-6}$ alkyl, especially methyl. Favourably, Z represents cyclobutyl.

When Y and Z are taken together with the two intervening carbon atoms to form a ring, representative compounds of use in the invention include those of structure IA to IL, especially IA to IK:

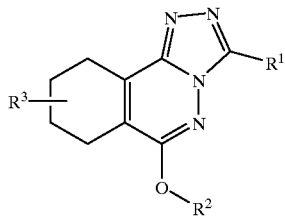
(IA)

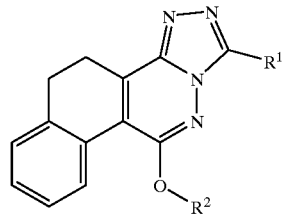
(IB)

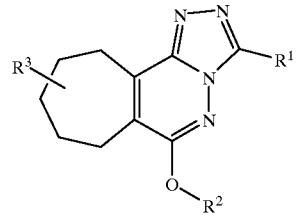
(IC)

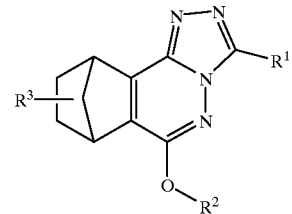
(ID)

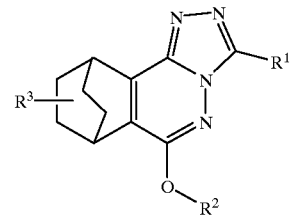
(IE)

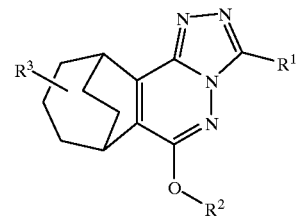
(IF)

-continued

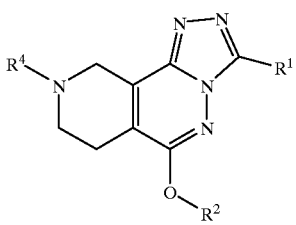
(IG)

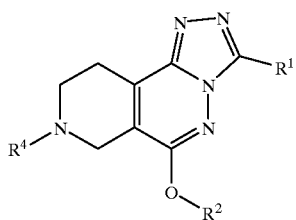
(IH)

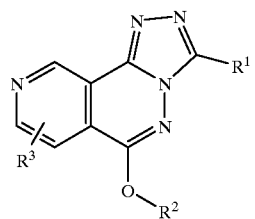
(IJ)

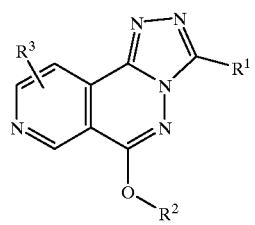
(IK)

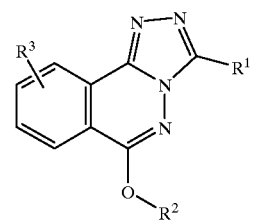
(IL)

wherein $R^1$ and $R^2$ are as defined above;

$R^3$ represents hydrogen, $C_{1-6}$ alkyl, aryl($C_{1-6}$)alkyl, halogen, cyano, hydroxy, hydroxymethyl or $C_{1-6}$ alkoxy; and $R^4$ represents hydrogen or $C_{1-6}$ alkyl.

Suitably, $R^3$ represents hydrogen or $C_{1-6}$ alkyl, especially hydrogen or methyl.

Suitably, $R^4$ represents hydrogen or methyl.

Favoured triazolo-pyridazine derivatives of use in the present invention include the compounds represented by formula IE as depicted above.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. Particular values include cyclopropyl, phenyl, methylphenyl, fluorophenyl, methoxyphenyl and pyridinyl.

More particularly, $R^1$ may represent unsubstituted or monosubstituted phenyl. Most particularly, $R^1$ represents phenyl.

Suitable values for the substituent $R^2$ in the compounds of use in the invention include cyanomethyl, hydroxybutyl, cyclohexylmethyl, propargyl, pyrrolidinylcarbonylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents. Typical values of $R^2$ include hydroxybutyl, cyclohexylmethyl, pyrrolidinylcarbonylmethyl, benzyl, pyrazolylmethyl, thiazolylmethyl, imidazolylmethyl, triazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$) alkyl. Illustrative substituents include $C_{1-6}$ alkyl, aryl($C_{1-6}$)alkyl, pyridyl($C_{1-6}$)alkyl, halogen, halo($C_{1-6}$)alkyl, cyano, cyano ($C_{1-6}$)alkyl, hydroxymethyl, $C_{1-6}$ alkoxy, $C_{3-7}$ cycloalkyl ($C_{1-6}$)alkoxy di($C_{1-6}$)alkylamino($C_{1-6}$)alkyl, di($C_{1-6}$) alkylaminocarbonyl($C_{1-6}$)alkyl and morpholinyl($C_{1-6}$)alkyl. Typical substituents include $C_{1-6}$ alkyl, aryl($C_{1-6}$)alkyl, halogen, cyano, hydroxymethyl, $C_{1-6}$ alkoxy and $C_{3-7}$ cycloalkyl($C_{1-6}$)alkoxy.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

More specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, dimethylaminoethyl, dimethylaminocarbonylmethyl and morpholinylmethyl.

Representative values of $R^2$ include cyanomethyl, hydroxybutyl, hydroxymethyl-cyclohexylmethyl, propargyl, dimethylaminomethyl-propargyl, dimethylmorpholinylmethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Illustrative values of $R^2$ include cyanomethyl, hydroxybutyl, hydroxymethyl-cyclohexylmethyl, propargyl, dimethylaminomethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, dimethylaminoethyl-triazolylmethyl, dimethylaminocarbonylmethyl-triazolylmethyl, morpholinylethyl-triazolylmethyl, methyl-tetrazolylmethyl, pyridinylmethyl, methyl-pyridinylmethyl, dimetthyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Particular values of $R^2$ include hydroxybutyl, hydroxymethyl-cyclohexylmethyl, pyrrolidinylcarbonylmethyl, cyanobenzyl, hydroxymethyl-benzyl, pyrazolylmethyl, dimethyl-pyrazolylmethyl, thiazolylmethyl, methyl-thiazolylmethyl, ethyl-thiazolylmethyl, imidazolylmethyl, methyl-imidazolylmethyl, ethyl-imidazolylmethyl, benzyl-imidazolylmethyl, methyl-triazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

A favoured value of $R^2$ is methyl-triazolylmethyl.

A particular sub-class of compounds of use in the invention is represented by the compounds of formula IIA, and pharmaceutically acceptable salts thereof and prodrugs thereof:

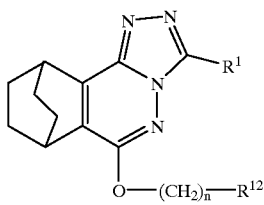

(IIA)

wherein $R^1$ is as defined above;

n is 1, 2, 3 or 4, typically 1; and $R^{12}$ represents hydroxy; or $C_{3-7}$ cycloalkyl, $C_{3-7}$ heterocycloalkylcarbonyl, aryl or heteroaryl, any of which groups may be optionally substituted.

Examples of optional substituents on the group R12 suitably include $C_{1-6}$ alkyl, aryl($C_{1-6}$)alkyl, halogen, cyano, hydroxymethyl, $C_{1-6}$ alkoxy and $C_{3-7}$ cycloalkyl($C_{1-6}$) alkoxy. Typical substituents include methyl, ethyl, benzyl, chloro, cyano, hydroxymethyl, ethoxy and cyclopropyl-methoxy.

Particular values of $R^{12}$ include hydroxy, hydroxymethyl-cyclohexyl, pyrrolidinylcarbonyl, cyanophenyl, hydroxymethyl-phenyl, pyrazolyl, dimethylpyrazolyl, thiazolyl, methylthiazolyl, ethylthiazolyl, imidazolyl, methylimidazolyl, ethylimidazolyl, benzylimidazolyl, methyltriazolyl, pyridinyl, methylpyridinyl, dimethyl-pyridinyl, ethoxypyridinyl, cyclopropylmethoxy-pyridinyl, pyridazinyl, chloropyridazinyl, pyrimidinyl, pyrazinyl, quinolinyl, isoquinolinyl and quinoxalinyl.

Another sub-class of compounds of use in the invention is represented by the compounds of formula IIB, and pharmaceutically acceptable salts thereof and prodrugs thereof:

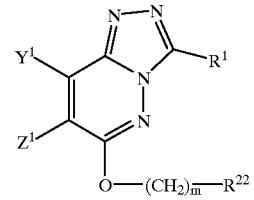

(IIB)

wherein $Y^1$ represents hydrogen or methyl;

$Z^1$ represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted;

$R^1$ is as defined with reference to formula I above;

m is 1 or 2, preferably 1; and $R^{22}$ represents aryl or heteroaryl, either of which groups may be optionally substituted.

Suitably, $Y^1$ represents hydrogen.

Examples of typical substituents on the group $Z^1$ include $C_{1-6}$ alkyl and halogen, especially methyl or chloro.

Representative values for the group $Z^1$ include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino.

Particular values for the group $Z^1$ include methyl, ethyl, isopropyl, tert-butyl, methyl-cyclopropyl, cyclobutyl, methyl-cyclobutyl, cyclopentyl, methyl-cyclopentyl, cyclohexyl, phenyl, pyrrolidinyl, methyl-pyrrolidinyl, piperidinyl, morpholinyl, thiomorpholinyl, pyridinyl, furyl, thienyl and chloro-thienyl.

A favoured value of $Z^1$ is cyclobutyl.

Examples of typical substituents on the group $R^{22}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl. Representative substituents include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, di($C_{1-6}$)alkylaminocarbonyl ($C_{1-6}$)alkyl and morpholinyl($C_{1-6}$)alkyl.

Illustrative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl.

Representative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, dimethylaminoethyl, dimethylaminocarbonylmethyl and morpholinylmethyl.

Particular values of $R^{22}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Specific values of $R^{22}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, dimethylaminoethyl-triazolyl, dimethylaminocarbonylmethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{22}$ is methyl-triazolyl.

A particular subset of the compounds of formula IIB above of use in the present invention is represented by the compounds of formula IIC, and pharmaceutically acceptable salts thereof:

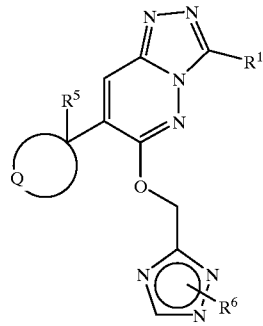

(IIC)

wherein $R^1$ is as defined with reference to formula I above;

Q represents the residue of a cyclopropyl, cyclobutyl, cyclopentyl or cyclohexyl ring;

$R^5$ represents hydrogen or methyl; and $R^6$ represents hydrogen or methyl.

In relation to formula IIC above, $R^1$ suitably represents phenyl.

In a favoured embodiment, Q suitably represents the residue of a cyclobutyl ring.

Suitably, $R^5$ represents hydrogen.

Suitably, $R^6$ represents methyl.

Specific compounds of use in the present invention include:

3-phenyl-6-(2-pyridyl)methyloxy-7,8,9,10-tetrahydro-(7,10-ethano)-1,2,4-triazolo [3,4-a]phthalazine;
3,7-diphenyl-6-(2-pyridyl)methyloxy-1,2,4-triazolo[4,3-b]pyridazine;
3-phenyl-6-(2-pyridyl)methyloxy-7,8,9,10-tetrahydro-1,2,4-triazolo[3,4-a]phthalazine;
7,8-dimethyl-3-phenyl-6-(2-pyridyl)methyloxy-1,2,4-triazolo[4,3-b]pyridazine;
7-methyl-3-phenyl-6-(2-pyridyl)methyloxy-1,2,4-triazolo[4,3-b]pyridazine;
7-ethyl-3-phenyl-6-(2-pyridyl)methyloxy-1,2,4-triazolo[4,3-b]pyridazine;
7,8-benzo-3-phenyl-6-(2-pyridyl)methyloxy-7,8,9,10-tetrahydro-1,2,4-triazolo[3,4-a]phthalazine;
8-methyl-3,7-diphenyl-6-(2-pyridyl)methyloxy-1,2,4-triazolo[4,3-b]pyridazine;
3-phenyl-6-(2-pyridyl)methyloxy-7,8,9,10-tetrahydro-(7,10-methano)-1,2,4-triazolo[3,4-a]phthalazine;
3-phenyl-5-(pyridin-2-ylmethoxy)-1,2,3a,4,7-pentaazacyclopenta-[α]naphthalene;
3-phenyl-5-(pyridin-2-ylmethoxy)-1,2,3a,4,8-pentaazacyclopenta-[α]naphthalene;
8-methyl-3-phenyl-6-(2-pyridyl)methyloxy-7,8,9,10-tetrahydro-1,2,4-triazolo[3,4-a]phthalazine;
3-phenyl-6-(2-pyridyl)methyloxy-(7,8-pentano)-1,2,4-triazolo[4,3-b]pyridazine;
8,8-dimethyl-3-phenyl-6-(2-pyridyl)methyloxy-7,8,9,10-tetrahydro-1,2,4-triazolo[3,4-a]phthalazine;
3-phenyl-7-(piperidin-1-yl)-6-(pyridin-2-ylmethoxy)-1,2,4-triazolo [4,3-b]pyridazine;
3-phenyl-7-(pyridin-4-yl)-6-(pyridin-2-ylmethoxy)-1,2,4-triazolo[4,3-b]pyridazine;
3-phenyl-5-(pyridin-2-ylmethoxy)-6,7,8,9-tetrahydro-1,2,3a,4,8-pentaazacyclopenta[a]naphthalene;
3-phenyl-5-(pyridin-2-ylmethoxy)-6,7,8,9-tetrahydro-1,2,3a,4,7-pentaazacyclopenta[a]naphthalene;
7-methyl-3-phenyl-5-(pyridin-2-ylmethoxy)-6,7,8,9-tetrahydro-1,2,3a,4,7-pentaazacyclopenta[a]naphthalene;
3-phenyl-6-(pyridin-2-ylmethoxy)-7-(thiophen-2-yl)-1,2,4-triazolo[4,3-b]pyridazine;
3-phenyl-6-(pyridin-2-ylmethoxy)-7-(thiophen-3-yl)-1,2,4-triazolo[4,3-b]pyridazine;
3-phenyl-6-(2-pyridyl)methyloxy-7,8,9,10-tetrahydro-(7,10-propano)-1,2,4-triazolo[3,4-a]phthalazine;
3-(4-methyl)phenyl-6-(2-pyridyl)methyloxy-7,8,9,10-tetrahydro-(7,10-ethano)-1,2,4-triazolo[3,4-a]phthalazine;
3-(3-methoxy)phenyl-6-(2-pyridyl)methyloxy-7,8,9,10-tetrahydro-(7,10-ethano)-1,2,4-triazolo[3,4-a]phthalazine;
3-(2-fluoro)phenyl-6-(2-pyridyl)methyloxy-7,8,9,10-tetrahydro-(7,10-ethano)-1,2,4-triazolo[3,4-a]phthalazine;
3-(3-pyridyl)-6-(2-pyridyl)methyloxy-7,8,9,10-tetrahydro-(7,10-ethano)-1,2,4-triazolo[3,4-a]phthalazine;
3-cyclopropyl-6-(2-pyridyl)methyloxy-7,8,9,10-tetrahydro-(7,10-ethano)-1,2,4-triazolo[3,4-a]phthalazine;
6-[(6-methyl)-2-pyridyl]methyloxy-3-phenyl-7,8,9,10-tetrahydro-(7,10-ethano)-1,2,4-triazolo[3,4-a]phthalazine;

6-[(3-methyl)-2-pyridyl]methyloxy-3-phenyl-7,8,9,10-tetrahydro-(7,10-ethano)-1,2,4-triazolo[3,4-a]phthalazine;
6-[(4-methyl)-2-pyridyl]methyloxy-3-phenyl-7,8,9,10-tetrahydro-(7,10-ethano)-1,2,4-triazolo[3,4-a]phthalazine;
6-[(5-methyl)-2-pyridyl]methyloxy-3-phenyl-7,8,9,10-tetrahydro-(7,10-ethano)-1,2,4-triazolo [3,4-a]phthalazine;
3-phenyl-6-(3-pyridyl)methyloxy-7,8,9,10-tetrahydro-(7,10-ethano)-1,2,4-triazolo[3,4-a]phthalazine;
3-phenyl-6-(4-pyridyl)methyloxy-7,8,9,10-tetrahydro-(7,10-ethano)-1,2,4-triazolo[3,4-a]phthalazine;
3-phenyl-6-[2-(1-methyl)imidazolyl]methyloxy-7,8,9,10-tetrahydro-(7,10-ethano)-1,2,4-triazolo[3,4-a]phthalazine;
6-(3-cyanophenyl)methyloxy-3-phenyl-7,8,9,10-tetrahydro-(7,10-ethano)-1,2,4-triazolo[3,4-a]phthalazine;
6-[1-(3,5-dimethyl)pyrazolyl]methyloxy-3-phenyl-7,8,9,10-tetrahydro-(7,10-ethano)-1,2,4-triazolo[3,4-a]phthalazine;
6-[4-(2-methyl)thiazolyl]methyloxy-3-phenyl-7,8,9,10-tetrahydro-(7,10-ethano)-1,2,4-triazolo[3,4-a]phthalazine;
3-phenyl-6-(2-quinoxalinyl)methyloxy-7,8,9,10-tetrahydro-(7,10-ethano)-1,2,4-triazolo[3,4-a]phthalazine;
3-phenyl-6-(3-pyridazinyl)methyloxy-7,8,9,10-tetrahydro-(7,10-ethano)-1,2,4-triazolo[3,4-a]phthalazine;
6-(1-benzylimidazol-2-yl)methyloxy-3-phenyl-7,8,9,10-tetrahydro-(7,10-ethano)-1,2,4-triazolo[3,4-a]phthalazine;
3-phenyl-6-(isoquinolin-1-yl)methyloxy-7,8,9,10-tetrahydro-(7,10-ethano)-1,2,4-triazolo[3,4-a]phthalazine;
6-(1-ethylimidazol-2-yl)methyloxy-3-phenyl-7,8,9,10-tetrahydro-(7,10-ethano)-1,2,4-triazolo[3,4-a]phthalazine;
3-phenyl-6-(1-pyrazolyl)methyloxy-7,8,9,10-tetrahydro-(7,10-ethano)-1,2,4-triazolo[3,4-a]phthalazine;
3-phenyl-6-(N-pyrrolidinylcarbonyl)methyloxy-7,8,9,10-tetrahydro-(7,10-ethano)-1,2,4-triazolo[3,4-a]phthalazine;
6-[4-(3-methyl)pyridyl]methyloxy-3-phenyl-7,8,9,10-tetrahydro-(7,10-ethano)-1,2,4-triazolo[3,4-a]phthalazine;
3-phenyl-6-(2-quinolinyl)methyloxy-7,8,9,10-tetrahydro-(7,10-ethano)-1,2,4-triazolo[3,4-a]phthalazine;
6-(2-imidazolyl)methyloxy-3-phenyl-7,8,9,10-tetrahydro-(7,10-ethano)-1,2,4-triazolo[3,4-a]phthalazine;
3-phenyl-6-(2-thiazolyl)methyloxy-7,8,9,10-tetrahydro-(7,10-ethano)-1,2,4-triazolo[3,4-a]phthalazine;
6-[2-(5-methyl)thiazolyl]methyloxy-3-phenyl-7,8,9,10-tetrahydro-(7,10-ethano)-1,2,4-triazolo[3,4-a]phthalazine;
6-[2-(4-methyl)thiazolyl]methyloxy-3-phenyl-7,8,9,10-tetrahydro-(7,10-ethano)-1,2,4-triazolo[3,4-a]phthalazine;
6-[2-(3,5-dimethyl)pyridyl]methyloxy-3-phenyl-7,8,9,10-tetrahydro-(7,10-ethano)-1,2,4-triazolo[3,4-a]phthalazine;
3-phenyl-6-(2-pyrazinyl)methyloxy-7,8,9,10-tetrahydro-(7,10-ethano)-1,2,4-triazolo[3,4-a]phthalazine;
6-[2-(4,6-dimethyl)pyridyl]methyloxy-3-phenyl-7,8,9,10-tetrahydro-(7,10-ethano)-1,2,4-triazolo[3,4-a]phthalazine;
3-phenyl-6-(4-thiazolyl)methyloxy-7,8,9,10-tetrahydro-(7,10-ethano)-1,2,4-triazolo[3,4-a]phthalazine;
6-[2-(5,6-dimethyl)pyridyl]methyloxy-3-phenyl-7,8,9,10-tetrahydro-(7,10-ethano)-1,2,4-triazolo[3,4-a]phthalazine;
6-(4-methylimidazol-2-yl)methyloxy-3-phenyl-7,8,9,10-tetrahydro-(7,10-ethano)-1,2,4-triazolo[3,4-a]phthalazine;
3-phenyl-6-(4-pyrimidinyl)methyloxy-7,8,9,10-tetrahydro-(7,10-ethano)-1,2,4-triazolo[3,4-a]phthalazine;
6-[4-(2-ethyl)thiazolyl]methyloxy-3-phenyl-7,8,9,10-tetrahydro-(7,10-ethano)-1,2,4-triazolo[3,4-a]phthalazine;
6-(6-chloropyridazin-3-yl)methyloxy-3-phenyl-7,8,9,10-tetrahydro-(7,10-ethano)-1,2,4-triazolo[3,4-a]phthalazine;
6-(2-imidazolyl)methyloxy-3-(4-methylphenyl)-7,8,9,10-tetrahydro-(7,10-ethano)-1,2,4-triazolo[3,4-a]phthalazine;
6-(4-hydroxymethylphenyl)methyloxy-3-phenyl-7,8,9,10-tetrahydro-(7,10-ethano)-1,2,4-triazolo[3,4-a]phthalazine;
6-(4-hydroxybutyl)oxy-3-phenyl-7,8,9,10-tetrahydro-(7,10-ethano)-1,2,4-triazolo[3,4-a]phthalazine;
6-(4-hydroxymethylcyclohexyl)methyloxy-3-phenyl-7,8,9,10-tetrahydro-(7,10-ethano)-1,2,4-triazolo[3,4-a]phthalazine;
6-(3-hydroxymethylphenyl)methyloxy-3-phenyl-7,8,9,10-tetrahydro-(7,10-ethano)-1,2,4-triazolo[3,4-a]phthalazine;
6-(1-methyl-1,2,4-triazol-3-yl)methyloxy-3-phenyl-7,8,9,10-tetrahydro-(7,10-ethano)-1,2,4-triazolo[3,4-a]phthalazine;
6-(2-methyl-1,2,4-triazol-3-yl)methyloxy-3-phenyl-7,8,9,10-tetrahydro-(7,10-ethano)-1,2,4-triazolo[3,4-a]phthalazine;
3-phenyl-6-(3-cyclopropylmethyloxy-2-pyridyl)methyloxy-7,8,9,10-tetrahydro-(7,10-ethano)-1,2,4-triazolo[3,4-a]phthalazine;
3-phenyl-6-(3-ethoxy-2-pyridyl)methyloxy-7,8,9,10-tetrahydro-(7,10-ethano)-1,2,4-triazolo[3,4-a]phthalazine;
6-(6-methylpyridin-2-yl)methyloxy-3-phenyl-1,2,4-triazolo[3,4-a]phthalazine;
6-(1-methyl-1H-1,2,4-triazol-3-ylmethoxy)-3,7-diphenyl-1,2,4-triazolo[4,3-b]pyridazine;
6-(2-methyl-2H-1,2,4-triazol-3-ylmethoxy)-3,7-diphenyl-1,2,4-triazolo[4,3-b]pyridazine;
3,7-diphenyl-6-(2H-1,2,4-triazol-3-ylmethoxy)-1,2,4-triazolo[4,3-b]pyridazine;
6-(2-methyl-2H-tetrazol-5-ylmethoxy)-3,7-diphenyl-1,2,4-triazolo[4,3-b]-pyridazine;
3,7-diphenyl-6-(2-propyl-2H-1,2,4-triazol-3-ylmethoxy)-1,2,4-triazolo[4,3-b]pyridazine;
3,7-diphenyl-6-(1-propyl-1H-1,2,4-triazol-3-ylmethoxy)-1,2,4-triazolo[4,3-b]pyridazine;
6-(1-methyl-1H-imidazol-4-ylmethoxy)-3,7-diphenyl-1,2,4-triazolo[4,3-b]pyridazine;
6-(3-methyl-3H-imidazol-4-ylmethoxy)-3,7-diphenyl-1,2,4-triazolo[4,3-b]pyridazine;
6-(4-methyl-4H-1,2,4-triazol-3-ylmethoxy)-3,7-diphenyl-1,2,4-triazolo[4,3-b]pyridazine;
6-(5-methyl-2H-1,2,4-triazol-3-ylmethoxy)-3,7-diphenyl-1,2,4-triazolo[4,3-b]pyridazine;
6-(3-methyl-3H-1,2,3-triazol-4-ylmethoxy)-3,7-diphenyl-1,2,4-triazolo[4,3-b]pyridazine;
3-(4-methoxyphenyl)-6-(1-methyl-1H-1,2,4-triazol-3-ylmethoxy)-7-phenyl-1,2,4-triazolo[4,3-b]pyridazine;
6-(3-methylpyridin-2-ylmethoxy)-3-phenyl-7-(piperidin-1-yl)-1,2,4-triazolo[4,3-b]pyridazine;

7-(morpholin-4-yl)-3-phenyl-6-(pyridin-2-ylmethoxy)-1,2,4-triazolo[4,3-b-]pyridazine;
3-phenyl-7-(pyridin-3-yl)-6-(pyridin-2-ylmethoxy)-1,2,4-triazolo[4,3-b]pyridazine;
8-methyl-6-(2-methyl-2H-1,2,4-triazol-3-ylmethoxy)-3,7-diphenyl-1,2,4-triazolo [4,3-b]pyridazine;
6-(1-methyl-1H-1,2,4-triazol-3-ylmethoxy)-7-(morpholin-4-yl)-3-phenyl-1,2,4-triazolo[4,3-b]pyridazine;
6-(2-methyl-2H-1,2,4-triazol-3-ylmethoxy)-7-(morpholin-4-yl)-3-phenyl-1,2,4-triazolo[4,3-b]pyridazine;
7-cyclohexyl-6-(2-methyl-2H-1,2,4-triazol-3-ylmethoxy)-3-phenyl-1,2,4-triazolo[4,3-b]pyridazine;
7-cyclohexyl-6-(1-methyl-1H-1,2,4-triazol-3-ylmethoxy)-3-phenyl-1,2,4-triazolo[4,3-b]pyridazine;
7-cyclopentyl-6-(2-methyl-2H-1,2,4-triazol-3-ylmethoxy)-3-phenyl-1,2,4-triazolo[4,3-b]pyridazine;
8-methyl-6-(1-methyl-1H-1,2,4-triazol-3-ylmethoxy)-3,7-diphenyl-1,2,4-triazolo[4,3-b]pyridazine;
7-cyclobutyl-6-(1-methyl-1H-1,2,4-triazol-3-ylmethoxy)-3-phenyl-1,2,4-triazolo [4,3-b]pyridazine;
7-tert-butyl-6-(2-methyl-2H-1,2,4-triazol-3-ylmethoxy)-3-phenyl-1,2,4-triazolo [4,3-b]pyridazine;
7-cyclobutyl-6-(2-methyl-2H-1,2,4-triazol-3-ylmethoxy)-3-phenyl-1,2,4-triazolo [4,3-b]pyridazine;
7-ethyl-6-(2-methyl-2H-1,2,4-triazol-3-ylmethoxy)-3-phenyl-1,2,4-triazolo[4,3-b]pyridazine;
7-tert-butyl-6-(1-methyl-1H-1,2,4-triazol-3-ylmethoxy)-3-phenyl-1,2,4-triazolo[4,3-b]pyridazine;
7-ethyl-6-(1-methyl-1H-1,2,4-triazol-3-ylmethoxy)-3-phenyl-1,2,4-triazolo[4,3-b]pyridazine;
7-methyl-6-(2-methyl-2H-1,2,4-triazol-3-ylmethoxy)-3-phenyl-1,2,4-triazolo [4,3-b]pyridazine;
7-(1-methyleyclobutyl)-6-(2-methyl-2H-1,2,4-triazol-3-ylmethoxy)-3-phenyl-1,2,4-triazolo[4,3-b]pyridazine;
7-methyl-6-(1-methyl-1H-1,2,4-triazol-3-ylmethoxy)-3-phenyl-1,2,4-triazolo [4,3-b]pyridazine;
7-cyclobutyl-3-phenyl-6-(2H-1,2,4-triazol-3-ylmethoxy)-1,2,4-triazolo[4,3-b]pyridazine;
7-cyclopentyl-6-(pyridin-2-ylmethoxy)-3-(thiophen-2-yl)-1,2,4-triazolo[4,3-b]pyridazine;
7-cyclopentyl-3-(2,4-difluorophenyl)-6-(1-methyl-1H-1,2,4-triazol-3-ylmethoxy)-1,2,4-triazolo[4,3-b]pyridazine;
7-cyclopentyl-6-(1-methyl-1H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(pyridin-4-yl)-1,2,4-triazolo[4,3-b]pyridazine;
7-cyclopentyl-3-(2-fluorophenyl)-6-(1-methyl-1H-1,2,4-triazol-3-ylmethoxy)-1, 2,4-triazolo[4,3-b]pyridazine;
7-cyclopentyl-3-(2-fluorophenyl)-6-(2-methyl-2H-1,2,4-triazol-3-ylmethoxy)-1,2,4-triazolo[4,3-b]pyridazine;
7-cyclopentyl-3-(2-fluorophenyl)-6-(pyridin-2-ylmethoxy)-1,2,4-triazolo[4,3-b]pyridazine;
7-cyclopentyl-3-(2,4-difluorophenyl)-6-(2-methyl-2H-1,2,4-triazol-3-ylmethoxy)-1,2,4-triazolo [4,3-b]pyridazine;
7-cyclopentyl-3-phenyl-6-(pyridin-2-ylmethoxy)-1,2,4-triazolo[4,3-b]pyridazine;
7-cyclopentyl-8-methyl-6-(2-methyl-2H-1,2,4-triazol-3-ylmethoxy)-3-phenyl-1,2,4-triazolo[4,3-b]pyridazine;
7-cyclopentyl-3-phenyl-6-(2H-1,2,4-triazol-3-ylmethoxy)-1,2,4-triazolo[4,3-b]pyridazine;
3-(4-methylphenyl)-7-phenyl-6-(pyridin-2-ylmethoxy)-1,2,4-triazolo[4,3-b]pyridazine;
3-(4-methylphenyl)-6-(3-methylpyridin-2-ylmethoxy)-7-phenyl-1,2,4-triazolo[4,3-b]pyridazine;
6-(1-ethyl-1H-imidazol-2-ylmethoxy)-3-(4-methylphenyl)-7-phenyl-1,2,4-triazolo[4,3-b]pyridazine;
3-phenyl-6-(pyridin-2-ylmethoxy)-7-(thiomorpholin-4-yl)-1,2,4-triazolo[4,3-b]pyridazine;
6-[2-(4-methylthiazol-5-yl)ethoxy]-3,7-diphenyl-1,2,4-triazolo[4,3-b]pyridazine;
(±)-7-(2-methylpyrrolidin-1-yl)-3-phenyl-6-(pyridin-2-ylmethoxy)-1,2,4-triazolo[4,3-b]pyridazine;
6-(1-methyl-1H-1,2,4-triazol-3-ylmethoxy)-3-phenyl-7-(pyridin-4-yl)-1,2,4-triazolo[4,3-b]pyridazine;
7-cyclopentyl-6-(1-methyl-1H-1,2,4-triazol-3-ylmethoxy)-3-phenyl-1,2,4-triazolo[4,3-b]pyridazine;
7-isopropyl-6-(1-methyl-1H-1,2,4-triazol-3-ylmethoxy)-3-phenyl-1,2,4-triazolo[4,3-b]pyridazine;
3-cyclopropyl-6-(1-methyl-1H-1,2,4-triazol-3-ylmethoxy)-7-phenyl-1,2,4-triazolo [4,3-b]pyridazine;
3-(2-fluorophenyl)-6-(2-methyl-2H-1,2,4-triazol-3-ylmethoxy)-7-phenyl-1,2,4-triazolo[4,3-b]pyridazine;
3-(2-fluorophenyl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(1-methyl-1H-1,2,4-triazol-3-ylmethoxy)-7-phenyl-3-(pyridin-3-yl)-1,2,4-triazolo[4,3-b]pyridazine;
6-(2-methyl-2H-1,2,4-triazol-3-ylmethoxy)-7-phenyl-3-(thiophen-2-yl)-1,2,4-triazolo[4,3-b]pyridazine;
6-(2-methyl-2H-1,2,4-triazol-3-ylmethoxy)-7-phenyl-3-(pyridin-3-yl)-1,2,4-triazolo[4,3-b)pyridazine;
3-(furan-3-yl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(5-methyl-1,2,4-oxadiazol-3-ylmethoxy)-3,7-diphenyl-1,2,4-triazolo[4,3-b]pyridazine;
7-phenyl-3-(thiophen-2-yl)-6-(2H-1,2,4-triazol-3-ylmethoxy)-1,2,4-triazolo[4,3-b]pyridazine;
3-(furan-2-yl)-6-(1-methyl-1H-1,2,4-triazol-3-ylmethoxy)-7-phenyl-1,2,4-triazolo [4,3-b]pyridazine;
6-(1-methyl-1H-1,2,4-triazol-3-ylmethoxy)-3-phenyl-7-(thiophen-3-yl)-1,2,4-triazolo[4,3-b]pyridazine;
6-(2-methyl-2H-1 ,2,4-triazol-3-ylmethoxy)-7-(thiophen-3-yl) -1,2,4-triazolo[4,3-b]pyridazine;
3-phenyl-7-(thiophen-3-yl)-6-(2H-1,2,4-triazol-3-ylmethoxy)-1,2,4-triazolo [4,3-b]pyridazine;
6-(2-methyl-2H-1,2,4-triazol-3-ylmethoxy)-3-phenyl-7-(thiophen-2-yl)-1,2,4-triazolo[4,3-b]pyridazine;
6-(1-methyl-1H-1,2,4-triazol-3-ylmethoxy)-3-phenyl-7-(thiophen-2-yl)-1,2,4-triazolo[4,3-b]pyridazine;
7-(furan-2-yl)-6-(2-methyl-2H-1,2,4-triazol-3-ylmethoxy)-3-phenyl-1,2,4-triazolo[4,3-b]pyridazine;
7-(furan-2-yl)-6-(1-methyl-1H-1,2,4-triazol-3-ylmethoxy)-3-phenyl-1,2,4-triazolo[4,3-b]pyridazine;
6-(3-methyl-1,2,4-oxadiazol-5-ylmethoxy)-3,7-diphenyl-1,2,4-triazolo[4,3-b]pyridazine;
3-(4-fluorophenyl)-6-(1-methyl-1H-1,2,4-triazol-3-ylmethoxy)-7-phenyl-1,2,4-triazolo[4,3-b]pyridazine;
3,7-diphenyl-6-(2H-1,2,3-triazol-4-ylmethoxy)-1,2,4-triazolo[4,3-b]pyridazine;
3,7-diphenyl-6-(pyrazin-2-ylmethoxy)-1,2,4-triazolo [4,3-b]pyridazine;
3-(4-methylphenyl)-6-(1-methyl-1H-1,2,4-triazol-3-ylmethoxy)-7-phenyl-1,2,4-triazolo[4,3-b]pyridazine;
6-(4-methylthiazol-2-ylmethoxy)-3,7-diphenyl-1,2,4-triazolo[4,3-b]pyridazine;
6-(5-methylthiazol-2-ylmethoxy)-3,7-diphenyl-1,2,4-triazolo[4,3-b]pyridazine;
3,7-diphenyl-6-(pyrimidin-4-ylmethoxy)-1,2,4-triazolo[4,3-b]pyridazine;
3,7-diphenyl-6-(pyridazin-3-ylmethoxy)-1,2,4-triazolo[4,3-b]pyridazine;

6-(1-methyl-1H-1,2,4-triazol-3-ylmethoxy)-7-(morpholin-4-yl)-3-(thiophen-2-yl)-1,2,4-triazolo[4,3-b]pyridazine;
3,7-diphenyl-6-(thiazol-4-ylmethoxy)-1,2,4-triazolo[4,3-b]pyridazine;
6-(5-methylisoxazol-3-ylmethoxy)-3,7-diphenyl-1,2,4-triazolo[4,3-b]pyridazine;
3-(3-fluorophenyl)-6-(1-methyl-1H-1,2,4-triazol-3-ylmethoxy)-7-(morpholin-4-yl) -1, 2,4-triazolo[4,3-b]pyridazine;
3,7-diphenyl-6-(pyrimidin-2-ylmethoxy)-1,2,4-triazolo[4,3-b]pyridazine;
6-(2-methyl-2H-1,2,3-triazol-4-ylmethoxy)-3,7-diphenyl-1,2,4-triazolo(4,3-b]pyridazine;
7-(1-methylcyclobutyl)-6-(1-methyl-1H-1,2,4-triazol-3-ylmethoxy)-3-phenyl-1,2,4-triazolo [4,3-b]pyridazine;
7-isopropyl-6-(2-methyl-2H-1,2,4-triazol-3-ylmethoxy)-3-phenyl-1,2,4-triazolo[4,3-b]pyridazine;
7-tert-butyl-3-(2-fluorophenyl)-6-(1-methyl-1H-1,2,4-triazol-3-ylmethoxy)-1,2,4-triazolo[4,3-b]pyridazine;
7-cyclopentyl-3-(4-methoxyphenyl)-6-(2-methyl-2H-1,2,4-triazol-3-ylmethoxy)-1,2,4-triazolo[4,3-b]pyridazine;
7-(1-methylcyclopentyl)-6-(1-methyl-1H-1,2,4-triazol-3-ylmethoxy)-3-phenyl-1,2,4-triazolo[4,3-b]pyridazine;
7-(1-methylcyclopentyl)-6-(2-methyl-2H-1,2,4-triazol-3-ylmethoxy)-3-phenyl-1,2,4-triazolo[4,3-b]pyridazine;
7-cyclopentyl-3-(furan-2-yl)-6-(2-methyl-2H-1,2,4-triazol-3-ylmethoxy)-1,2,4-triazolo[4,3-b]pyridazine;
7-cyclopentyl-3-(furan-2-yl)-6-(1-methyl-1H-1,2,4-triazol-3-ylmethoxy)-1,2,4-triazolo[4,3-b]pyridazine;
3-(3,7-diphenyl-1,2,4-triazolo[4,3-b]pyridazin-6-yloxymethyl)-1,2,4-triazol-1-ylacetonitrile;
7-(1-methylcyclopropyl)-6-(2-methyl-2H-1,2,4-triazol-3-ylmethoxy)-3-phenyl-1,2,4-triazolo[4,3-b]pyridazine;
7-(1-methylcyclopropyl)-6-(1-methyl-1H-1,2,4-triazol-3-ylmethoxy)-3-phenyl-1,2,4-triazolo(4,3-b]pyridazine;
3-(3-fluorophenyl)-6-(1-methyl-1H-1,2,4-triazol-3-ylmethoxy)-7-phenyl-1,2,4-triazolo[4,3-b]pyridazine;
7-(1-methylcyclopentyl)-6-(3-methylpyridin-2-ylmethoxy)-3-phenyl-1,2,4-triazolo[4,3-b]pyridazine;
6-(1-methyl-1H-1,2,3-triazol-4-ylmethoxy)-3,7-diphenyl-1,2,4-triazolo[4,3-b]pyridazine;
3-(5-methylthiophen-2-yl)-6-(1-methyl-1H-1,2,4-triazol-3-ylmethoxy)-7-phenyl-1,2,4-triazolo[4,3-b]pyridazine;
2-[3-(3,7-diphenyl-1,2,4-triazolo[4,3-b]pyridazin-6-yloxymethyl)-1,2,4-triazol-1-yl] -N,N-dimethylacetamide;
3,7-diphenyl-6-[1-(pyridin-2-ylmethyl)-1H-1,2,4-triazol-3-ylmethoxy]-1,2,4-triazolo[4,3-b]pyridazine;
6-(1-benzyl-1H-1,2,4-triazol-3-ylmethoxy)-3,7-diphenyl-1,2,4-triazolo[4,3-b]pyridazine;
2-[5-(3,7-diphenyl-1, 2,4-triazolo[4,3-b]pyridazin-6-yloxymethyl)-1,2,4-triazol-1-yl]acetamide;
N-[2-[3-(3,7-diphenyl-1,2,4-triazolo[4,3-b]pyridazin-6-yloxymethyl)-1,2,4-triazol-1-yl]ethyl]-N,N-dimethylamine;
3,7-diphenyl-6-(pyrimidin-5-ylmethoxy)-1,2,4-triazolo[4,3-b]pyridazine;
6-[1-(2-(morpholin-4-yl)-ethyl)-1H-1,2,4-triazol-3-ylmethoxy]-3,7-diphenyl-1,2,4-triazolo[4,3-b]pyridazine;
6-(2-methyl-2H-1,2,4-triazol-3-ylmethoxy)-3-phenyl-7-(pyrrolidin-1-yl)-1,2,4-triazolo[4,3-b]pyridazine;
7-(5-chlorothiophen-2-yl)-6-(2-methyl-2H-1,2,4-triazol-3-ylmethoxy)-3-phenyl-1,2,4-triazolo[4,3-b]pyridazine;
7-(5-chlorothiophen-2-yl)-6-(1-methyl-1H-1,2,4-triazol-3-ylmethoxy)-3-phenyl-1,2,4-triazolo[4,3-b]pyridazine;
6-(1H-benzimidazol-2-ylmethoxy)-3-(2,4-difluorophenyl)-7-(1-methylcyclopentyl)-1,2,4-triazolo[4,3-b]pyridazine;
3-(furan-3-yl)-6-(2-pyridyl)methyloxy-7,8,9,10-tetrahydro-1,2,4-triazolo[3,4-a]phthalazine;
7-cyclobutyl-3-phenyl-6-(prop-2-ynyloxy)-1,2,4-triazolo[4,3-b]pyridazine;
(7-cyclobutyl-3-phenyl-1,2,4-triazolo[4,3-b]pyridazin-6-yloxy)acetonitrile;
N-[4-(7-cyclobutyl-3-phenyl-1,2,4-triazolo[4,3-b]pyridazin-6-yloxy)but-2-ynyl]-N,N-dimethylamine;
2-[3-(3,7-diphenyl-1,2,4-triazolo[4,3-b]pyridazin-6-yloxymethyl)-1,2,4-triazol-1-yl]ethylamine;
3,7-diphenyl-6-[1-(2-(pyrrolidin-1-yl)ethyl)-1H-1,2,4-triazol-3-ylmethoxy]-1,2,4-triazolo [4,3-b]pyridazine;
6-[1-(1-methylpiperidin-4-yl)-1H-1,2,4-triazo1-3-ylmethoxy]-3,7-diphenyl-1,2,4-triazolo[4,3-b]pyridazine;
3,7-diphenyl-6-[1-(2-(piperazin-1-yl)ethyl)- H-1,2,4-triazol-3-ylmethoxyl-1,2,4-triazolo[4,3-b]pyridazine;
7-(1-methylcyclopentyl)-6-(2-methyl-2H-1,2,4-triazol-3-ylmethoxy)-3-(2,4-difluorophenyl)-1,2,4-triazolo[4,3-b]pyridazine;
7-(cyclobut-1-enyl)-6-(2-methyl-2H-1,2,4-triazol-3-ylmethoxy)-3-phenyl-1,2,4-triazolo[4,3-b]pyridazine;
7-(furan-3-yl)-6-(1-methyl-1H-1,2,4-triazol-3-ylmethoxy)-3-phenyl-1,2,4-triazolo [4,3-b]pyridazine;
N,N-diethyl-N-[6-(1-methyl-11H-I1,2,4-triazol-3-ylmethoxy)-3-phenyl-1,2,4-triazolo [4,3-b]pyridazin-7-yl]amine;
7-(1-methylcyclopentyl)-6-(1-methyl-1H-1,2,4-triazol-3-ylmethoxy)-3-(2,4-difluorophenyl)-1,2,4-triazolo[4,3-b]pyridazine;
7-(1,1-dimethylpropyl)-6-(1-methyl-1H-1,2,4-triazol-3-ylmethoxy)-3-phenyl-1,2,4-triazolo[4,3-b]pyridazine;
6-(2-methyl-2H-1,2,4-triazol-3-ylmethoxy)-3-(4-fluorophenyl)-7-(thiophen-3-yl)-1, 2,4-triazolo[4,3-b]pyridazine;
6-(1-methyl-1H-1,2,4-triazol-3-ylmethoxy)-3-(4-fluorophenyl)-7-(thiophen-3-yl)-1,2,4-triazolo[4,3-b]pyridazine;
6-(2-methyl-2H-1,2,4-triazol-3-ylmethoxy)-3-(2-fluorophenyl)-7-(thiophen-3-yl)-1,2,4-triazolo[4,3-b]pyridazine;
3-(2-fluorophenyl)-7-(-methylcyclobutyl)-6-(2-methyl-2H-1,2,4-triazol-3-ylmethoxy)-1,2,4-triazolo[4,3-b]pyridazine;
3-(2-fluorophenyl)-7-(1-methylcyclobutyl)-6-(1-methyl-1H-1,2,4-triazol-3-ylmethoxy)-1,2,4-triazolo[4,3-b]pyridazine;
6-(1-methyl-11H-1,2,4-triazol-3-ylmethoxy)-3-(2-fluorophenyl)-7-(thiophen-3-yl)-1,2,4-triazolo[4,3-b]pyridazine;
8-methyl-7-(1-methylcyclobutyl)-6-(1- methyl- H-1,2,4-triazol-3-ylmethoxy)-3-phenyl-1,2,4-triazolo[4,3-b)pyridazine;
8-methyl-7-(-methylcyclobutyl)-6-(2-methyl-2H-1,2,4-triazol-3-ylmethoxy)-3-phenyl-1,2,4-triazolo[4,3-b]pyridazine;
6-(1-methyl-1H-1,2,4-triazol-3-ylmethoxy)-3-phenyl-7-(pyrrolidin-1-yl)-1,2,4-triazolo[4,3-b]pyridazine;
7-cyclobutyl-8-methyl-6-(2-methyl-2H-1,2,4-triazol-3-ylmethoxy)-3-phenyl-1,2,4-triazolo[4,3-b]pyridazine;
7-cyclobutyl-8-methyl-6-(1-methyl-1H-1,2,4-triazol-3-ylmethoxy)-3-phenyl-1,2,4-triazolo[4,3-b]pyridazine;
7-(1-methylcyclopentyl)-6-(2-methyl-2H-1,2,4-triazol-3-ylmethoxy)-3-(2-fluorophenyl)-1,2,4-triazolo[4,3-b]pyridazine;
7-(1-methylcyclopentyl)-6-(1-methyl-1H-1,2,4-triazol-3-ylmethoxy)-3-(2-fluorophenyl)-1,2,4-triazolo[4,3-b]pyridazine;

7-cyclobutyl-6-[4-(2,6-dimethylmorpholin-4-yl)but-2-ynyloxy]-3-phenyl-1,2,4-triazolo[4,3-b]pyridazine;
and pharmaceutically acceptable salts thereof and prodrugs thereof.

In another aspect, the present invention provides a method for the treatment and/or prevention of psychotic disorders including schizophrenia, with substantially no sedation, which comprises administering to a patient in need of such treatment an effective amount of a compound which is a modulator of the benzodiazepine binding site of the human $GABA_A$ receptor, having a binding affinity ($K_i$) for the α3 subunit of the human $GABA_A$ receptor of 10 nM or less, which elicits at least a 40% potentiation of the GABA $EC_{20}$ response in stably transfected recombinant cell lines expressing the α3 subunit of the human $GABA_A$ receptor, and which elicits at most a 30% potentiation of the GABA $EC_{20}$ response in stably transfected cell lines expressing the α1 subunit of the human $GABA_A$ receptor.

This aspect of the present invention also provides the use of a compound which is a modulator of the benzodiazepine binding site of the human $GABA_A$ receptor, having a binding affinity ($K_i$) for the α3 subunit of the human $GABA_A$ receptor of 10 nM or less, which elicits at least a 40% potentiation of the GABA $EC_{20}$ response in stably transfected recombinant cell lines expressing the α3 subunit of the human $GABA_A$ receptor, and which elicits at most a 30% potentiation of the GABA $EC_{20}$ response in stably transfected cell lines expressing the α1 subunit of the human $GABA_A$ receptor, for the manufacture of a medicament for the treatment and/or prevention of psychotic disorders including schizophrenia, with substantially no sedation.

In this aspect of the invention, the binding affinity ($K_i$) of compounds for the α3 subunit of the human $GABA_A$ receptor is conveniently as measured in the assay described hereinbelow. The α3 subunit binding affinity ($K_i$) of compounds of use in this aspect of the invention is 10 nM or less, preferably 2 nM or less, and more preferably 1 nM or less.

In this aspect of the invention, the potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds of use in this aspect of the invention will elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of use in this aspect of the invention will elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

In order to elicit their behavioural effects, the compounds of use in this aspect of the invention will be brain-penetrant; in other words, these compounds will be capable of crossing the so-called "blood-brain barrier". Preferably, the compounds of use in this aspect of the invention will be capable of exerting their beneficial therapeutic action following administration by the oral route.

A representative compound of use in this aspect of the invention is 7-cyclobutyl-6-(2-methyl-2H-1,2,4-triazol-3-ylmethoxy)-3-phenyl-1,2,4-triazolo [4,3-b]pyridazine.

For therapeutic application, pharmaceutical compositions may be provided which comprise one or more compounds of use in this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of use in the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical compositions in liquid form may be adapted for administration orally or by injection and may include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds of use in this invention may be co-administered with another anti-schizophrenic medicament, for example one producing its effects via dopamine $D_2$ and/or 5-$HT_2$ receptor blockade. In such circumstances, an enhanced anti-schizophrenic effect may be envisaged without a corresponding increase in sedation and/or extrapyramidal side-effects (movement disorders) such as may be caused by, for example, $D_2$ receptor subtype blockade; or a comparable anti-schizophrenic effect with reduced side-effects may alternatively be envisaged. Such co-administration may be desirable where a patient is already established on a treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

The compounds of formula I of use in the present invention, including the specific compounds disclosed above, may be prepared by the processes described in WO 98/04559.

The compounds of use in this invention potently inhibit the binding of [$^3$M-flumazenil to the benzodiazepine binding site of human $GABA_A$ receptors containing the α2 or α3 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1 β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The specific compounds listed above were tested in the above assay, and all were found to possess a $K_i$ value for displacement of [$^3$H]-flumazenil from the α2 and/or α3 subunit of the human $GABA_A$ receptor of 100 nM or less.

What is claimed is:

1. A method for the treatment of schizophrenia, which comprises administering to a patient in need of such treatment an effective amount of a compound of formula I, or a pharmaceutically acceptable salt thereof:

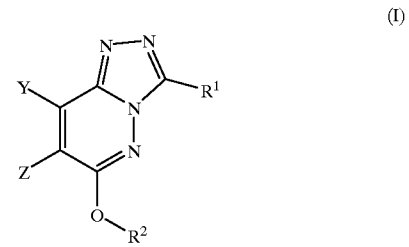

wherein

Y represents hydrogen or $C_{1-6}$alkyl; and

Z represents $C_{1-6}$alkyl, $C_{3-7}$cycloalkyl, $C_{4-7}$cycloalkenyl, aryl, $C_{3-7}$heterocycloalkyl, heteroaryl or di($C_{1-6}$)alkylamino, any of which groups may be optionally substituted with one or more $C_{1-6}$alkyl, aryl($_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmopholinyl($C_{1-6}$)alkyl or imidazolyl($C_{1-6}$)alkyl substituents; or Y and Z are taken together with the two intervening carbon atoms to form a ring selected from $C_{5-9}$cycloalkenyl, $C_{6-10}$-bicycloalkenyl, tetrahydropyridinyl, pyridinyl and phenyl, any of which rings may be optionally benzo-fused and/or substituted with one or more $C_{1-6}$alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmopholinyl($C_{1-6}$)alkyl or imidazolyl($C_{1-6}$)alkyl substituents;

$R^1$ represents $C_{3-7}$cycloalkyl, phenyl, furyl, thienyl or pyridinyl, any of which groups may be optionally substituted with one or more $C_{1-6}$alkyl, aryl($_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalyl($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmopholinyl($C_{1-6}$)alkyl or imidazolyl($C_{1-6}$)alkyl substituents; and $R^2$ represents cyano($C_{1-6}$)alkyl, propargyl, $C_{3-7}$heterocycloalkylcarbonyl($C_{1-6}$)alkyl, aryl($C_{1-6}$)alkyl or heteroaryl($C_{1-6}$)alkyl, any of which groups may be optionally substituted with one or more $C_{1-6}$alkyl, aryl($_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalyl($C_{1-6}$)alkoxy, $C_{3-7}$cycloalkoxy, amino($C_{1-6}$)alkyl, di($C_{1-6}$)

alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmopholinyl($C_{1-6}$)alkyl or imidazolyl($C_{1-6}$)alkyl substituents.

2. A method according to claim 1 wherein the compound administered is represented by formula IIA, and pharmaceutically acceptable salts thereof:

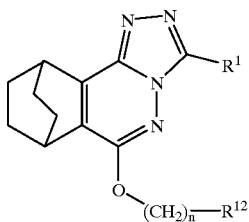

(IIA)

wherein $R^1$ is as defined in claim 1;

n is 1,2,3 or 4;

$R^{12}$ represents hydroxy; or $C_{3-7}$cycloalkyl, $C_{3-7}$heterocycloalkylcarbonyl, aryl or heteroaryl, any of which groups may be optionally substituted with one or more $C_{1-6}$alkyl, aryl($C_{1-6}$)alkyl, halogen, cyano, hydroxymethyl, $C_{1-6}$alkoxy, $C_{3-7}$cycloalkyl($C_{1-6}$)alkoxy, substituents.

3. A method according to claim 1 wherein the compound administered is represented by formula IIB, and pharmaceutically acceptable salts thereof:

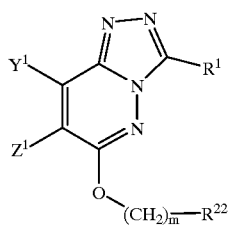

(IIB)

wherein $Y^1$ represents hydrogen or methyl;

$Z^1$ represents $C_{1-6}$alkyl, $C_{3-7}$cycloalkyl, $C_{4-7}$cycloalkenyl, aryl, $C_{3-7}$heterocycloalkyl, heteroaryl or di($C_{1-6}$) alkylamino, any of which groups may be optionally substituted with $C_{1-6}$alkyl or halogen substituents;

$R^1$ is as defined in claim 1;

m is 1 or 2; and $R^{22}$ represents aryl or heteroaryl, either of which groups may be optionally substituted with one or more $C_{1-6}$alkyl, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-7}$cycloalkyl($C_{1-6}$)alkoxy, di($C_{1-6}$)alkylamino($C_{1-6}$) alkyl, amino($C_{1-6}$)alkyl, di($C_{1-6}$)alkylaminocarbonyl ($C_{1-6}$)alkyl, N-($C_{1-6}$)alkylpiperidinyl, pyrrolidinyl($C_{1-6}$)alkyl, piperazinyl($C_{1-6}$)alkyl, or morpholinyl($C_{1-6}$)alkyl substituents.

4. A method according to claim 3 wherein the compound administered is represented by formula IIC, and pharmaceutically acceptable salts thereof:

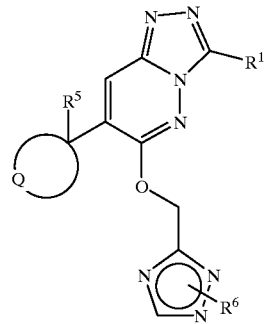

(IIC)

wherein $R^1$ is as defined in claim 1;

Q represents the residue of a cyclopropyl, cyclobutyl, cyclopentyl or cyclohexyl ring;

$R^5$ represents hydrogen or methyl; and $R^6$ represents hydrogen or methyl.

5. A method according to claim 1 wherein the compound administered is selected from:

3-phenyl-6-(2-pyridyl)methyloxy-7,8,9,10-tetrahydro-(7, 10-ethano)-1,2,4-triazolo [3,4-a]phthalazine;

3,7-diphenyl-6-(2-pyridyl)methyloxy-1,2,4-triazolo[4,3-b] pyridazine;

3-phenyl-6-(2-pyridyl)methyloxy-7,8,9,10-tetrahydro-1,2, 4-triazolo[3,4-a]phthalazine;

7,8-dimethyl-3-phenyl-6-(2-pyridyl)methyloxy-1,2,4-triazolo[4,3-b]pyridazine;

7-methyl-3-phenyl-6-(2-pyridyl)methyloxy-1,2,4-triazolo [4,3-b]pyridazine;

7-ethyl-3-phenyl-6-(2-pyridyl)methyloxy-1,2,4-triazolo [4,3-b]pyridazine;

7,8-benzo-3-phenyl-6-(2-pyridyl)methyloxy-7,8,9,10-tetrahydro-1,2,4-triazolo[3,4-a]phthalazine;

8-methyl-3,7-diphenyl-6-(2-pyridyl)methyloxy-1,2,4-triazolo[4,3-b]pyridazine;

3-phenyl-6-(2-pyridyl)methyloxy-7,8,9,10-tetrahydro-(7, 10-methano)-1,2,4-triazolo[3,4-a]phthalazine;

3-phenyl-5-(pyridin-2-ylmethoxy)-1,2,3a,4,7-pentaazacyclopenta-[α]naphthalene;

3-phenyl-5-(pyridin-2-ylmethoxy)-1,2,3a,4,8-pentaazacyclopenta-[α]naphthalene;

8-methyl-3-phenyl-6-(2-pyridyl)methyloxy-7,8,9,10-tetrahydro-1,2,4-triazolo[3,4-a]phthalazine;

3-phenyl-6-(2-pyridyl)methyloxy-(7,8-pentano)-1,2,4-triazolo[4,3-b]pyridazine;

8,8-dimethyl-3-phenyl-6-(2-pyridyl)methyloxy-7,8,9,10-tetrahydro-1,2,4-triazolo[3,4-a]phthalazine;

3-phenyl-7-(piperidin-1-yl)-6-(pyridin-2-ylmethoxy)-1,2,4-triazolo [4,3-b]pyridazine;

3-phenyl-7-(pyridin-4-yl)-6-(pyridin-2-ylmethoxy)-1,2,4-triazolo[4,3-b]pyridazine;

3-phenyl-5-(pyridin-2-ylmethoxy)-6,7,8,9-tetrahydro-1,2, 3a,4,8-pentaazacyclopenta[a]naphthalene;

3-phenyl-5-(pyridin-2-ylmethoxy)-6,7,8,9-tetrahydro-1,2, 3a,4,7-pentaazacyclopenta[a]naphthalene;

7-methyl-3-phenyl-5-(pyridin-2-ylmethoxy)-6,7,8,9-tetrahydro-1,2,3a,4,7-pentaazacyclopenta[a]naphthalene;

3-phenyl-6-(pyridin-2-ylmethoxy)-7-(thiophen-2-yl)-1,2,4-triazolo[4,3-b]pyridazine;

3-phenyl-6-(pyridin-2-ylmethoxy)-7-(thiophen-3-yl)-1,2,4-triazolo[4,3-b[pyridazine;

3-phenyl-6-(2-pyridyl)methyloxy-7,8,9,10-tetrahydro-(7, 10-propano)-1,2,4-triazolo[3,4-a]phthalazine;

3-(4-methyl)phenyl-6-(2-pyridyl)methyloxy-7,8,9,10-
tetrahydro-(7,10-ethano)-1,2,4-triazolo[3,4-a]
phthalazine;
3-(3-methoxy)phenyl-6-(2-pyridyl)methyloxy-7,8,9,10-
tetrahydro-(7,10-ethano)-1,2,4-triazolo[3,4-a]
phthalazine;
3-(2-fluoro)phenyl-6-(2-pyridyl)methyloxy-7,8,9,10-
tetrahydro-(7,10-ethano)-1,2,4-triazolo[3,4-a]
phthalazine;
3-(3-pyridyl)-6-(2-pyridyl)methyloxy-7,8,9,10-tetrahydro-
(7,10-ethano)-1,2,4-triazolo[3,4-a]phthalazine;
3-cyclopropyl-6-(2-pyridyl)methyloxy-7,8,9,10-tetrahydro-
(7,10-ethano)-1,2,4-triazolo[3,4-a]phthalazine;
6-[(6-methyl)-2-pyridyl]methyloxy-3-phenyl-7,8,9,10-
tetrahydro-(7,10-ethano)-1,2,4-triazolo[3,4-a]
phthalazine;
6-[(3-methyl)-2-pyridyl]methyloxy-3-phenyl-7,8,9,10-
tetrahydro-(7,10-ethano)-1,2,4-triazolo[3,4-a]
phthalazine;
6-[(4-methyl)-2-pyridyl]methyloxy-3-phenyl-7,8,9,10-
tetrahydro-(7,10-ethano)-1, 2,4-triazolo[3,4-a]
phthalazine;
6-[(5-methyl)-2-pyridyl]methyloxy-3-phenyl-7,8,9,10-
tetrahydro-(7,10-ethano)-1,2,4-triazolo [3,4-a]
phthalazine;
3-phenyl-6-(3-pyridyl)methyloxy-7,8,9,10-tetrahydro-(7,
10-ethano)-1,2,4-triazolo[3,4-a]phthalazine;
3-phenyl-6-(4-pyridyl)methyloxy-7,8,9,10-tetrahydro-(7,
10-ethano)-1,2,4-triazolo[3,4-a]phthalazine;
3-phenyl-6-[2-(1-methyl)imidazolyl]methyloxy-7,8,9,10-
tetrahydro-(7,10-ethano)-1,2,4-triazolo[3,4-a]
phthalazine;
6-(3-cyanophenyl)methyloxy-3-phenyl-7,8,9,10-tetrahydro-
(7,10-ethano)-1,2,4-triazolo[3,4-a]phthalazine;
6-[1-(3,5-dimethyl)pyrazolyl]methyloxy-3-phenyl-7,8,9,10-
tetrahydro-(7,10-ethano)-1,2,4-triazolo[3,4-a]
phthalazine;
6-[4-(2-methyl)thiazolyl]methyloxy-3-phenyl-7,8,9,10-
tetrahydro-(7,10-ethano)-1,2,4-triazolo[3,4-a]
phthalazine;
3-phenyl-6-(2-quinoxalinyl)methyloxy-7,8,9,10-tetrahydro-
(7,10-ethano)-1,2,4-triazolo[3,4-a]phthalazine;
3-phenyl-6-(3-pyridazinyl)methyloxy-7,8,9,10-tetrahydro-
(7,10-ethano)-1,2,4-triazolo[3,4-a]phthalazine;
6-(1-benzylimidazol-2-yl)methyloxy-3-phenyl-7,8,9,10-
tetrahydro-(7,10-ethano)-1,2,4-triazolo[3,4-a]
phthalazine;
3-phenyl-6-(isoquinolin-1-yl)methyloxy-7,8,9,10-
tetrahydro-(7,10-ethano)-1,2,4-triazolo[3,4-a]
phthalazine;
6-(1-ethylimidazol-2-yl)methyloxy-3-phenyl-7,8,9,10-
tetrahydro-(7,10-ethano)-1,2,4-triazolo[3,4-a]
phthalazine;
3-phenyl-6-(1-pyrazolyl)methyloxy-7,8,9,10-tetrahydro-(7,
10-ethano)-1,2,4-triazolo[3,4-a]phthalazine;
3-phenyl-6-(N-pyrrolidinylcarbonyl)methyloxy-7,8,9,10-
tetrahydro-(7,10-ethano)-1,2,4-triazolo[3,4-a]
phthalazine;
6-[4-(3-methyl)pyridyl]methyloxy-3-phenyl-7,8,9,10-
tetrahydro-(7,10-ethano)-1,2,4-triazolo[3,4-
a]phthalazine;
3-phenyl-6-(2-quinolinyl)methyloxy-7,8,9,10-tetrahydro-
(7,10-ethano)-1,2,4-triazolo[3,4-a]phthalazine;
6-(2-imidazolyl)methyloxy-3-phenyl-7,8,9,10-tetrahydro-
(7,10-ethano)-1,2,4-triazolo[3,4-a]phthalazine;
3-phenyl-6-(2-thiazolyl)methyloxy-7,8,9,10-tetrahydro-(7,
10-ethano)-1,2,4-triazolo[3,4-a]phthalazine;
6-[2-(5-methyl)thiazolyl]methyloxy-3-phenyl-7,8,9,10-
tetrahydro-(7,10-ethano)-1,2,4-triazolo[3,4-a]
phthalazine;
6-[2-(4-methyl)thiazolyl]methyloxy-3-phenyl-7,8,9,10-
tetrahydro-(7,10-ethano)-1,2,4-triazolo[3,4-a]
phthalazine;
6-[2-(3,5-dimethyl)pyridyl]methyloxy-3-phenyl-7,8,9,10-
tetrahydro-(7,10-ethano)-1,2,4-triazolo[3,4-a]
phthalazine;
3-phenyl-6-(2-pyrazinyl)methyloxy-7,8,9,10-tetrahydro-(7,
10-ethano)-1,2,4-triazolo[3,4-a]phthalazine;
6-[2-(4,6-dimethyl)pyridyl]methyloxy-3-phenyl-7,8,9,10-
tetrahydro-(7,10-ethano)-1,2,4-triazolo[3,4-a]
phthalazine;
3-phenyl-6-(4-thiazolyl)methyloxy-7,8,9,10-tetrahydro-(7,
10-ethano)-1,2,4-triazolo[3,4-a]phthalazine;
6-[2-(5,6-dimethyl)pyridyl]methyloxy-3-phenyl-7,8,9,10-
tetrahydro-(7,10-ethano)-1,2,4-triazolo[3,4-a]
phthalazine;
6-(4-methylimidazol-2-yl)methyloxy-3-phenyl-7,8,9,10-
tetrahydro-(7,10-ethano)-1,2,4-triazolo[3,4-a]
phthalazine;
3-phenyl-6-(4-pyrimidinyl)methyloxy-7,8,9,10-tetrahydro-
(7,10-ethano)-1,2,4-triazolo[3,4-a]phthalazine;
6-[4-(2-ethyl)thiazolyl]methyloxy-3-phenyl-7,8,9,10-
tetrahydro-(7,10-ethano)-1,2,4-triazolo[3,4-a]
phthalazine;
6-(6-chloropyridazin-3-yl)methyloxy-3-phenyl-7,8,9,10-
tetrahydro-(7,10-ethano)-1,2,4-triazolo[3,4-a]
phthalazine;
6-(2-imidazolyl)methyloxy-3-(4-methylphenyl)-7,8,9,10-
tetrahydro-(7,10-ethano)-1,2,4-triazolo[3,4-a]
phthalazine;
6-(4-hydroxymethylphenyl)methyloxy-3-phenyl-7,8,9,10-
tetrahydro-(7,10-ethano)-1,2,4-triazolo[3,4-a]
phthalazine;
6-(4-hydroxybutyl)oxy-3-phenyl-7,8,9,10-tetrahydro-(7,10-
ethano)-1,2,4-triazolo[3,4-a]phthalazine;
6-(4-hydroxymethylcyclohexyl)methyloxy-3-phenyl-7,8,9,
10-tetrahydro-(7,10-ethano)-1,2,4-triazolo[3,4-a]
phthalazine;
6-(3-hydroxymethylphenyl)methyloxy-3-phenyl-7,8,9,10-
tetrahydro-(7,10-ethano)-1,2,4-triazolo[3,4-a]
phthalazine;
6-(1-methyl-1,2,4-triazol-3-yl)methyloxy-3-phenyl-7,8,9,
10-tetrahydro-(7,10-ethano)-1,2,4-triazolo[3,4-a]
phthalazine;
6-(2-methyl-1,2,4-triazol-3-yl)methyloxy-3-phenyl-7,8,9,
10-tetrahydro-(7,10-ethano)-1,2,4-triazolo[3,4-a]
phthalazine;
3-phenyl-6-(3-cyclopropylmethyloxy-2-pyridyl)methyloxy-
7,8,9,10-tetrahydro-(7,10-ethano)-1,2,4-triazolo[3,4-a]
phthalazine;
3-phenyl-6-(3-ethoxy-2-pyridyl)methyloxy-7,8,9,10-
tetrahydro-(7,10-ethano)-1,2,4-triazolo[3,4-a]
phthalazine;
6-(6-methylpyridin-2-yl)methyloxy-3-phenyl-1,2,4-triazolo
[3,4-a]phthalazine;
6-(1-methyl-1H-1,2,4-triazol-3-ylmethoxy)-3,7-diphenyl-1,
2,4-triazolo[4,3-b]pyridazine;
6-(2-methyl-2H-1,2,4-triazol-3-ylmethoxy)-3,7-diphenyl-1,
2,4-triazolo[4,3-b]pyridazine;
3,7-diphenyl-6-(2H-1,2,4-triazol-3-ylmethoxy)-1,2,4-
triazolo[4,3-b]pyridazine;
6-(2-methyl-2H-tetrazol-5-ylmethoxy)-3,7-diphenyl-1,2,4-
triazolo[4,3-b]-pyridazine;
3,7-diphenyl-6-(2-propyl-2H-1,2,4-triazol-3-ylmethoxy)-1,
2,4-triazolo[4,3-b]pyridazine;

3,7-diphenyl-6-(1-propyl-1H-1,2,4-triazol-3-ylmethoxy)-1,2,4-triazolo[4,3-b]pyridazine;
6-(1-methyl-1H-imidazol-4-ylmethoxy)-3,7-diphenyl-1,2,4-triazolo[4,3-b]pyridazine;
6-(3-methyl-3H-imidazol-4-ylmethoxy)-3,7-diphenyl-1,2,4-triazolo[4,3-b]pyridazine;
6-(4-methyl-4H-1,2,4-triazol-3-ylmethoxy)-3,7-diphenyl-1,2,4-triazolo[4,3-b]pyridazine;
6-(5-methyl-2H-1,2,4-triazol-3-ylmethoxy)-3,7-diphenyl-1,2,4-triazolo[4,3-b]pyridazine;
6-(3-methyl-3H-1,2,3-triazol-4-ylmethoxy)-3,7-diphenyl-1,2,4-triazolo[4,3-b]pyridazine;
3-(4-methoxyphenyl)-6-(1-methyl-1H-1,2,4-triazol-3-ylmethoxy)-7-phenyl-1,2,4-triazolo[4,3-b]pyridazine;
6-(3-methylpyridin-2-ylmethoxy)-3-phenyl-7-(piperidin-1-yl)-1,2,4-triazolo[4,3-b]pyridazine;
7-(morpholin-4-yl)-3-phenyl-6-(pyridin-2-ylmethoxy)-1,2,4-triazolo[4,3-b-]pyridazine;
3-phenyl-7-(pyridin-3-yl)-6-(pyridin-2-ylmethoxy)-1,2,4-triazolo[4,3-b]pyridazine;
8-methyl-6-(2-methyl-2H-1,2,4-triazol-3-ylmethoxy)-3,7-diphenyl-1,2,4-triazolo [4,3-b]pyridazine;
6-(1-methyl-1H-1,2,4-triazol-3-ylmethoxy)-7-(morpholin-4-yl)-3-phenyl-1,2,4-triazolo[4,3-b]pyridazine;
6-(2-methyl-2H-1,2,4-triazol-3-ylmethoxy)-7-(morpholin-4-yl)-3-phenyl-1,2,4-triazolo[4,3-b]pyridazine;
7-cyclohexyl-6-(2-methyl-2H-1,2,4-triazol-3-ylmethoxy)-3-phenyl-1,2,4-triazolo[4,3-b]pyridazine;
7-cyclohexyl-6-(1-methyl-1H-1,2,4-triazol-3-ylmethoxy)-3-phenyl-1,2,4-triazolo[4,3-b]pyridazine;
7-cyclopentyl-6-(2-methyl-2H-1,2,4-triazol-3-ylmethoxy)-3-phenyl-1,2,4-triazolo[4,3-b]pyridazine;
8-methyl-6-(1-methyl-1H-1,2,4-triazol-3-ylmethoxy)-3,7-diphenyl-1,2,4-triazolo[4,3-b]pyridazine;
7-cyclobutyl-6-(1-methyl-1H-1,2,4-triazol-3-ylmethoxy)-3-phenyl-1,2,4-triazolo [4,3-b]pyridazine;
7-tert-butyl-6-(2-methyl-2H-1,2,4-triazol-3-ylmethoxy)-3-phenyl-1,2,4-triazolo [4,3-b]pyridazine;
7-cyclobutyl-6-(2-methyl-2H-1,2,4-triazol-3-ylmethoxy)-3-phenyl-1,2,4-triazolo [4,3-b]pyridazine;
7-ethyl-6-(2-methyl-2H-1,2,4-triazol-3-ylmethoxy)-3-phenyl-1,2,4-triazolo[4,3-b]pyridazine;
7-tert-butyl-6-(1-methyl-1H-1,2,4-triazol-3-ylmethoxy)-3-phenyl-1,2,4-triazolo[4,3-b]pyridazine;
7-ethyl-6-(1-methyl-1H-1,2,4-triazol-3-ylmethoxy)-3-phenyl-1,2,4-triazolo[4,3-b]pyridazine;
7-methyl-6-(2-methyl-2H-1,2,4-triazol-3-ylmethoxy)-3-phenyl-1,2,4-triazolo [4,3-b]pyridazine;
7-(1-methyleyclobutyl)-6-(2-methyl-2H-1,2,4-triazol-3-ylmethoxy)-3-phenyl-1,2,4-triazolo[4,3-b]pyridazine;
7-methyl-6-(1-methyl-1H-1,2,4-triazol-3-ylmethoxy)-3-phenyl-1,2,4-triazolo [4,3-b]pyridazine;
7-cyclobutyl-3-phenyl-6-(2H-1,2,4-triazol-3-ylmethoxy)-1,2,4-triazolo[4,3-b]pyridazine;
7-cyclopentyl-6-(pyridin-2-ylmethoxy)-3-(thiophen-2-yl)-1,2,4-triazolo[4,3-b]pyridazine;
7-cyclopentyl-3-(2,4-difluorophenyl)-6-(1-methyl-1H-1,2,4-triazol-3-ylmethoxy)-1,2,4-triazolo[4,3-b]pyridazine;
7-cyclopentyl-6-(1-methyl-1H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(pyridin-4-yl)-1,2,4-triazolo[4,3-b]pyridazine;
7-cyclopentyl-3-(2-fluorophenyl)-6-(1-methyl-1H-1,2,4-triazol-3-ylmethoxy)-1, 2,4-triazolo[4,3-b]pyridazine;
7-cyclopentyl-3-(2-fluorophenyl)-6-(2-methyl-2H-1,2,4-triazol-3-ylmethoxy)-1,2,4-triazolo[4,3-b]pyridazine;
7-cyclopentyl-3-(2-fluorophenyl)-6-(pyridin-2-ylmethoxy)-1,2,4-triazolo[4,3-b]pyridazine;
7-cyclopentyl-3-(2,4-difluorophenyl)-6-(2-methyl-2H-1,2,4-triazol-3-ylmethoxy)-1,2,4-triazolo [4,3-b]pyridazine;
7-cyclopentyl-3-phenyl-6-(pyridin-2-ylmethoxy)-1,2,4-triazolo[4,3-b]pyridazine;
7-cyclopentyl-8-methyl-6-(2-methyl-2H-1,2,4-triazol-3-ylmethoxy)-3-phenyl-1,2,4-triazolo[4,3-b]pyridazine;
7-cyclopentyl-3-phenyl-6-(2H-1,2,4-triazol-3-ylmethoxy)-1,2,4-triazolo[4,3-b]pyridazine;
3-(4-methylphenyl)-7-phenyl-6-(pyridin-2-ylmethoxy)-1,2,4-triazolo[4,3-b]pyridazine;
3-(4-methylphenyl)-6-(3-methylpyridin-2-ylmethoxy)-7-phenyl-1,2,4-triazolo[4,3-b]pyridazine;
6-(1-ethyl-1H-imidazol-2-ylmethoxy)-3-(4-methylphenyl)-7-phenyl-1,2,4-triazolo[4,3-b]pyridazine;
3-phenyl-6-(pyridin-2-ylmethoxy)-7-(thiomorpholin-4-yl)-1,2,4-triazolo[4,3-b]pyridazine;
6-[2-(4-methylthiazol-5-yl)ethoxy]-3,7-diphenyl-1,2,4-triazolo[4,3-b]pyridazine;
(±)-7-(2-methylpyrrolidin-1-yl)-3-phenyl-6-(pyridin-2-ylmethoxy)-1,2,4-triazolo[4,3-b]pyridazine;
6-(1-methyl-1H-1,2,4-triazol-3-ylmethoxy)-3-phenyl-7-(pyridin-4-yl)-1,2,4-triazolo[4,3-b]pyridazine;
7-cyclopentyl-6-(1-methyl-1H-1,2,4-triazol-3-ylmethoxy)-3-phenyl-1,2,4-triazolo[4,3-b]pyridazine;
7-isopropyl-6-(1-methyl-1H-1,2,4-triazol-3-ylmethoxy)-3-phenyl-1,2,4-triazolo[4,3-b]pyridazine;
3-cyclopropyl-6-(1-methyl-1H-1,2,4-triazol-3-ylmethoxy)-7-phenyl-1,2,4-triazolo [4,3-b]pyridazine;
3-(2-fluorophenyl)-6-(2-methyl-2H-1,2,4-triazol-3-ylmethoxy)-7-phenyl-1,2,4-triazolo[4,3-b]pyridazine;
3-(2-fluorophenyl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(1-methyl-1H-1,2,4-triazol-3-ylmethoxy)-7-phenyl-3-(pyridin-3-yl)-1,2,4-triazolo[4,3-b]pyridazine;
6-(2-methyl-2H-1,2,4-triazol-3-ylmethoxy)-7-phenyl-3-(thiophen-2-yl)-1,2,4-triazolo[4,3-b]pyridazine;
6-(2-methyl-2H-1,2,4-triazol-3-ylmethoxy)-7-phenyl-3-(pyridin-3-yl)-1,2,4-triazolo[4,3-b)pyridazine;
3-(furan-3-yl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(5-methyl-1,2,4-oxadiazol-3-ylmethoxy)-3,7-diphenyl-1,2,4-triazolo[4,3-b]pyridazine;
7-phenyl-3-(thiophen-2-yl)-6-(2H-1,2,4-triazol-3-ylmethoxy)-1,2,4-triazolo[4,3-b]pyridazine;
3-(furan-2-yl)-6-(1-methyl-1H-1,2,4-triazol-3-ylmethoxy)-7-phenyl-1,2,4-triazolo [4,3-b]pyridazine;
6-(1-methyl-1H-1,2,4-triazol-3-ylmethoxy)-3-phenyl-7-(thiophen-3-yl)-1,2,4-triazolo[4,3-b]pyridazine;
6-(2-methyl-2H-1,2,4-triazol-3-ylmethoxy)-7-(thiophen-3-yl)-1,2,4-triazolo[4,3-b]pyridazine;
3-phenyl-7-(thiophen-3-yl)-6-(2H-1,2,4-triazol-3-ylmethoxy)-1,2,4-triazolo [4,3-b]pyridazine;
6-(2-methyl-2H-1,2,4-triazol-3-ylmethoxy)-3-phenyl-7-(thiophen-2-yl)-1,2,4-triazolo[4,3-b]pyridazine;
6-(1-methyl-1H-1,2,4-triazol-3-ylmethoxy)-3-phenyl-7-(thiophen-2-yl)-1,2,4-triazolo[4,3-b]pyridazine;
7-(furan-2-yl)-6-(2-methyl-2H-1,2,4-triazol-3-ylmethoxy)-3-phenyl-1,2,4-triazolo[4,3-b]pyridazine;
7-(furan-2-yl)-6-(1-methyl-1H-1,2,4-triazol-3-ylmethoxy)-3-phenyl-1,2,4-triazolo[4,3-b]pyridazine;
6-(3-methyl-1,2,4-oxadiazol-5-ylmethoxy)-3,7-diphenyl-1,2,4-triazolo[4,3-b]pyridazine;

3-(4-fluorophenyl)-6-(1-methyl-1H-1,2,4-triazol-3-ylmethoxy)-7-phenyl-1,2,4-triazolo[4,3-b]pyridazine;

3,7-diphenyl-6-(2H-1,2,3-triazol-4-ylmethoxy)-1,2,4-triazolo[4,3-b]pyridazine;

3,7-diphenyl-6-(pyrazin-2-ylmethoxy)-1,2,4-triazolo [4,3-b]pyridazine;

3-(4-methylphenyl)-6-(1-methyl-1H-1,2,4-triazol-3-ylmethoxy)-7-phenyl-1,2,4-triazolo[4,3-b]pyridazine;

6-(4-methylthiazol-2-ylmethoxy)-3,7-diphenyl-1,2,4-triazolo[4,3-b]pyridazine;

6-(5-methylthiazol-2-ylmethoxy)-3,7-diphenyl-1,2,4-triazolo[4,3-b]pyridazine;

3,7-diphenyl-6-(pyrimidin-4-ylmethoxy)-1,2,4-triazolo[4,3-b]pyridazine;

3,7-diphenyl-6-(pyridazin-3-ylmethoxy)-1,2,4-triazolo[4,3-b]pyridazine;

6-(1-methyl-1H-1,2,4-triazol-3-ylmethoxy)-7-(morpholin-4-yl)-3-(thiophen-2-yl)-1,2,4-triazolo[4,3-b]pyridazine;

3,7-diphenyl-6-(thiazol-4-ylmethoxy)-1,2,4-triazolo[4,3-b]pyridazine;

6-(5-methylisoxazol-3-ylmethoxy)-3,7-diphenyl-1,2,4-triazolo[4,3-b]pyridazine;

3-(3-fluorophenyl)-6-(1-methyl-1H-1,2,4-triazol-3-ylmethoxy)-7-(morpholin-4-yl) -1, 2,4-triazolo[4,3-b]pyridazine;

3,7-diphenyl-6-(pyrimidin-2-ylmethoxy)-1,2,4-triazolo[4,3-b]pyridazine;

6-(2-methyl-2H-1,2,3-triazol-4-ylmethoxy)-3,7-diphenyl-1,2,4-triazolo(4,3-b]pyridazine;

7-(1-methylcyclobutyl)-6-(1-methyl-1H-1,2,4-triazol-3-ylmethoxy)-3-phenyl-1,2,4-triazolo [4,3-b]pyridazine;

7-isopropyl-6-(2-methyl-2H-1,2,4-triazol-3-ylmethoxy)-3-phenyl-1,2,4-triazolo[4,3-b]pyridazine;

7-tert-butyl-3-(2-fluorophenyl)-6-(1-methyl-1H-1,2,4-triazol-3-ylmethoxy)-1,2,4-triazolo[4,3-b]pyridazine;

7-cyclopentyl-3-(4-methoxyphenyl)-6-(2-methyl-2H-1,2,4-triazol-3-ylmethoxy)-1,2,4-triazolo[4,3-b]pyridazine;

7-(1-methylcyclopentyl)-6-(1-methyl-1H-1,2,4-triazol-3-ylmethoxy)-3-phenyl-1,2,4-triazolo[4,3-b]pyridazine;

7-(1-methylcyclopentyl)-6-(2-methyl-2H-1,2,4-triazol-3-ylmethoxy)-3-phenyl-1,2,4-triazolo[4,3-b]pyridazine;

7-cyclopentyl-3-(furan-2-yl)-6-(2-methyl-2H-1,2,4-triazol-3-ylmethoxy)-1,2,4-triazolo[4,3-b]pyridazine;

7-cyclopentyl-3-(furan-2-yl)-6-(1-methyl-1H-1,2,4-triazol-3-ylmethoxy)-1,2,4-triazolo[4,3-b]pyridazine;

3-(3,7-diphenyl-1,2,4-triazolo[4,3-b]pyridazin-6-yloxymethyl)-1,2,4-triazol-1-ylacetonitrile;

7-(1-methylcyclopropyl)-6-(2-methyl-2H-1,2,4-triazol-3-ylmethoxy)-3-phenyl-1,2,4-triazolo[4,3-b]pyridazine;

7-(1-methylcyclopropyl)-6-(1-methyl-1H-1,2,4-triazol-3-ylmethoxy)-3-phenyl-1,2,4-triazolo(4,3-b]pyridazine;

3-(3-fluorophenyl)-6-(1-methyl-1H-1,2,4-triazol-3-ylmethoxy)-7-phenyl-1,2,4-triazolo[4,3-b]pyridazine;

7-(1-methylcyclopentyl)-6-(3-methylpyridin-2-ylmethoxy)-3-phenyl-1,2,4-triazolo[4,3-b]pyridazine;

6-(1-methyl-1H-1,2,3-triazol-4-ylmethoxy)-3,7-diphenyl-1,2,4-triazolo[4,3-b]pyridazine;

3-(5-methylthiophen-2-yl)-6-(1-methyl-1H-1,2,4-triazol-3-ylmethoxy)-7-phenyl-1,2,4-triazolo[4,3-b]pyridazine;

2-[3-(3,7-diphenyl-1,2,4-triazolo[4,3-b]pyridazin-6-yloxymethyl)-1,2,4-triazol-1-yl] -N,N-dimethylacetamide;

3,7-diphenyl-6-[1-(pyridin-2-ylmethyl)-1H-1,2,4-triazol-3-ylmethoxy]-1,2,4-triazolo[4,3-b]pyridazine;

6-(1-benzyl-1H-1,2,4-triazol-3-ylmethoxy)-3,7-diphenyl-1,2,4-triazolo[4,3-b]pyridazine;

2-[5-(3,7-diphenyl-1, 2,4-triazolo[4,3-b]pyridazin-6-yloxymethyl)-1,2,4-triazol-1-yl]acetamide;

N-[2-[3-(3,7-diphenyl-1,2,4-triazolo[4,3-b]pyridazin-6-yloxymethyl)-1,2,4-triazol-1-yl]ethyl]-N,N-dimethylamine;

3,7-diphenyl-6-(pyrimidin-5-ylmethoxy)-1,2,4-triazolo[4,3-b]pyridazine;

6-[1-(2-(morpholin-4-yl)-ethyl)-1H-1,2,4-triazol-3-ylmethoxy]-3,7-diphenyl-1,2,4-triazolo[4,3-b]pyridazine;

6-(2-methyl-2H-1,2,4-triazol-3-ylmethoxy)-3-phenyl-7-(pyrrohidin-1-yl)-1,2,4-triazolo[4,3-b]pyridazine;

7-(5-chlorothiophen-2-yl)-6-(2-methyl-2H-1,2,4-triazol-3-ylmethoxy)-3-phenyl-1,2,4-triazolo[4,3-b]pyridazine;

7-(5-chlorothiophen-2-yl)-6-(1-methyl-1H-1,2,4-triazol-3-ylmethoxy)-3-phenyl-1,2,4-triazolo[4,3-b]pyridazine;

6-(1H-benzimidazol-2-ylmethoxy)-3-(2,4-difluorophenyl)-7-(1-methylcyclopentyl)-1,2,4-triazolo[4,3-b]pyridazine;

3-(furan-3-yl)-6-(2-pyridyl)methyloxy-7,8,9,10-tetrahydro-1,2,4-triazolo[3,4-a]phthalazine;

7-cyclobutyl-3-phenyl-6-(prop-2-ynyloxy)-1,2,4-triazolo[4,3-b]pyridazine;

(7-cyclobutyl-3-phenyl-1,2,4-triazolo[4,3-b]pyridazin-6-yloxy)acetonitrile;

N-[4-(7-cyclobutyl-3-phenyl-1,2,4-triazolo[4,3-b]pyridazin-6-yloxy)but-2-ynyl]-N,N-dimethylamine;

2-[3-(3,7-diphenyl-1,2,4-triazolo[4,3-b]pyridazin-6-yloxymethyl)-1,2,4-triazol-1-yl]ethylamine;

3,7-diphenyl-6-[1-(2-(pyrrolidin-1-yl)ethyl)-1H-1,2,4-triazol-3-ylmethoxy]-1,2,4-triazolo [4,3-b]pyridazine;

6-[1-(1-methylpiperidin-4-yl)-1H-1,2,4-triazo1-3-ylmethoxy]-3,7-diphenyl-1,2,4-triazolo[4,3-b]pyridazine;

3,7-diphenyl-6-[1-(2-(piperazin-1-yl)ethyl)- H-1,2,4-triazol-3-ylmethoxyl-1,2,4-triazolo[4,3-b]pyridazine;

7-(1-methylcyclopentyl)-6-(2-methyl-2H-1,2,4-triazol-3-ylmethoxy)-3-(2,4-difluorophenyl)-1,2,4-triazolo[4,3-b]pyridazine;

7-(cyclobut-1-enyl)-6-(2-methyl-2H-1,2,4-triazol-3-ylmethoxy)-3-phenyl-1,2,4-triazolo[4,3-b]pyridazine;

7-(furan-3-yl)-6-(1-methyl-1H-1,2,4-triazol-3-ylmethoxy)-3-phenyl-1,2,4-triazolo [4,3-b]pyridazine;

N,N-diethyl-N-[6-(1-methyl-11H-I1,2,4-triazol-3-ylmethoxy)-3-phenyl-1,2,4-triazolo [4,3-b]pyridazin-7-yl]amine;

7-(1-methylcyclopentyl)-6-(1-methyl-1H-1,2,4-triazol-3-ylmethoxy)-3-(2,4-difluorophenyl)-1,2,4-triazolo[4,3-b]pyridazine;

7-(1,1-dimethylpropyl)-6-(1-methyl-1H-1,2,4-triazol-3-ylmethoxy)-3-phenyl-1,2,4-triazolo[4,3-b]pyridazine;

6-(2-methyl-2H-1,2,4-triazol-3-ylmethoxy)-3-(4-fluorophenyl)-7-(thiophen-3-yl)-1, 2,4-triazolo[4,3-b]pyridazine;

6-(1-methyl-1H-1,2,4-triazol-3-ylmethoxy)-3-(4-fluorophenyl)-7-(thiophen-3-yl)-1,2,4-triazolo[4,3-b]pyridazine;

6-(2-methyl-2H-1,2,4-triazol-3-ylmethoxy)-3-(2-fluorophenyl)-7-(thiophen-3-yl)-1,2,4-triazolo[4,3-b]pyridazine;

3-(2-fluorophenyl)-7-(-methylcyclobutyl)-6-(2-methyl-2H-1,2,4-triazol-3-ylmethoxy)-1,2,4-triazolo[4,3-b]pyridazine;

3-(2-fluorophenyl)-7-(1-methylcyclobutyl)-6-(1-methyl-1H-1,2,4-triazol-3-ylmethoxy)-1,2,4-triazolo[4,3-b]pyridazine;

6-(1-methyl-11H-1,2,4-triazol-3-ylmethoxy)-3-(2-fluorophenyl)-7-(thiophen-3-yl)-1,2,4-triazolo[4,3-b]pyridazine;

8-methyl-7-(1-methylcyclobutyl)-6-(1- methyl- H-1,2,4-triazol-3-ylmethoxy)-3-phenyl-1,2,4-triazolo[4,3-b)pyridazine;

8-methyl-7-(-methylcyclobutyl)-6-(2-methyl-2H-1,2,4-triazol-3-ylmethoxy)-3-phenyl-1,2,4-triazolo[4,3-b]pyridazine;

6-(1-methyl-1H-1,2,4-triazol-3-ylmethoxy)-3-phenyl-7-(pyrrolidin-1-yl)-1,2,4-triazolo[4,3-b]pyridazine;

7-cyclobutyl-8-methyl-6-(2-methyl-2H-1,2,4-triazol-3-ylmethoxy)-3-phenyl-1,2,4-triazolo[4,3-b]pyridazine;

7-cyclobutyl-8-methyl-6-(1-methyl-1H-1,2,4-triazol-3-ylmethoxy)-3-phenyl-1,2,4-triazolo[4,3-b]pyridazine;

7-(1-methylcyclopentyl)-6-(2-methyl-2H-1,2,4-triazol-3-ylmethoxy)-3-(2-fluorophenyl)-1,2,4-triazolo[4,3-b]pyridazine;

7-(1-methylcyclopentyl)-6-(1-methyl-1H-1,2,4-triazol-3-ylmethoxy)-3-(2-fluorophenyl)-1,2,4-triazolo[4,3-b]pyridazine;

7-cyclobutyl-6-[4-(2,6-dimethylmorpholin-4-yl)but-2-ynyloxy]-3-phenyl-1,2,4-triazolo[4,3-b]pyridazine;

and pharmaceutically acceptable salts thereof and prodrugs thereof.

6. A method for the treatment of schizophrenia, with substantially no sedation, which comprises administering to a patient in need of such treatment an effective amount of a compound which is a modulator of the benzodiazepine binding site of the human $GABA_A$ receptor, having a binding affinity ($K_i$) for the α3 subunit of the human $GABA_A$ receptor of 10 nM or less, which elicits at least a 40% potentiation of the GABA $EC_{20}$ response in stably transfected recombinant cell lines expressing the α3 subunit of the human $GABA_A$ receptor, and which elicits at most a 30% potentiation of the GABA $EC_{20}$ response in stably transfected cell lines expressing the α1 subunit of the human $GABA_A$ receptor.

7. A method for the treatment of schizophrenia, which comprises administering to a patient in need of such treatment an effective amount of 7-cyclobutyl-6-(2-methyl-2H-1,2,4-triazol-3-ylmethyoxy)-3-phenyl-1,2,4-triazolo[4,3-b]pyridazine.

8. A pharmaceutical composition comprising a compound of formula I as defined in claim 1, or a pharmaceutically acceptable salt thereof, in association with a further antipsychotic medicament.

9. A composition as claimed in claim 8 wherein the further antipsychotic medicament is selected from haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

* * * * *